(12) United States Patent
Tanaka

(10) Patent No.: US 11,423,552 B2
(45) Date of Patent: Aug. 23, 2022

(54) INFORMATION PROCESSING APPARATUS, SYSTEM, METHOD, AND STORAGE MEDIUM TO COMPARE IMAGES

(71) Applicant: CANON KABUSHIKI KAISHA, Tokyo (JP)

(72) Inventor: Toru Tanaka, Chofu (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/952,717

(22) Filed: Apr. 13, 2018

(65) Prior Publication Data

US 2018/0300888 A1 Oct. 18, 2018

(30) Foreign Application Priority Data

Apr. 13, 2017 (JP) .............................. JP2017-079433

(51) Int. Cl.
| | | |
|---|---|---|
| *G06T 15/00* | (2011.01) | |
| *G06T 7/33* | (2017.01) | |
| *G06T 7/00* | (2017.01) | |
| *G06T 7/62* | (2017.01) | |
| *G06T 7/73* | (2017.01) | |
| *G16H 30/40* | (2018.01) | |
| *G16H 40/63* | (2018.01) | |
| *G16H 30/20* | (2018.01) | |

(52) U.S. Cl.
CPC .............. *G06T 7/33* (2017.01); *G06T 7/0014* (2013.01); *G06T 7/62* (2017.01); *G06T 7/73* (2017.01); *G16H 30/20* (2018.01); *G16H 30/40* (2018.01); *G16H 40/63* (2018.01); *G06T 2207/10012* (2013.01); *G06T 2207/10072* (2013.01); *G06T 2207/30096* (2013.01)

(58) Field of Classification Search
None
See application file for complete search history.

(56) References Cited

U.S. PATENT DOCUMENTS

| | | | | |
|---|---|---|---|---|
| 5,874,961 A | * | 2/1999 | Bates .................. | G06F 3/04855 715/786 |
| 5,930,809 A | | 7/1999 | Middlebrook | |
| 6,147,683 A | * | 11/2000 | Martinez ............. | G06F 3/04855 715/786 |

(Continued)

FOREIGN PATENT DOCUMENTS

| | | |
|---|---|---|
| CN | 101420900 A | 4/2009 |
| CN | 106413510 A | 2/2017 |

(Continued)

*Primary Examiner* — Anh-Tuan V Nguyen
(74) *Attorney, Agent, or Firm* — Canon U.S.A., Inc. IP Division

(57) ABSTRACT

Based on information regarding positions of two-dimensional images included in a first three-dimensional image and two-dimensional images included in a second three-dimensional image, an information processing apparatus acquires information regarding a first range, which is a range of positions where the two-dimensional images included in the first three-dimensional image are present, and a second range, which is a range of positions where the two-dimensional images included in the second three-dimensional image are present, and displays, on a display unit, a figure indicating the first range such that an area, in the first range, included in the second range is distinguishable.

17 Claims, 12 Drawing Sheets

(56) References Cited

U.S. PATENT DOCUMENTS

| | | | |
|---|---|---|---|
| 6,590,595 B1* | 7/2003 | Wagner | G06F 3/04855 715/784 |
| 7,765,491 B1 | 7/2010 | Cotterill | |
| 8,160,676 B2 | 4/2012 | Gielen et al. | |
| 8,265,354 B2 | 9/2012 | Zhang et al. | |
| 9,724,177 B2* | 8/2017 | Levin | A61B 1/00045 |
| 10,290,059 B2* | 5/2019 | Basu | G06Q 40/06 |
| 2002/0090119 A1* | 7/2002 | Saito | G16H 40/63 382/128 |
| 2003/0095697 A1* | 5/2003 | Wood | A61B 6/032 382/131 |
| 2004/0242988 A1* | 12/2004 | Niwa | G06F 3/0304 600/407 |
| 2004/0264753 A1* | 12/2004 | Capolunghi | G06T 19/00 382/128 |
| 2006/0268117 A1* | 11/2006 | Loui | H04N 5/77 348/220.1 |
| 2007/0186171 A1* | 8/2007 | Junuzovic | G06F 3/0481 715/751 |
| 2007/0195092 A1* | 8/2007 | Abshear | G06T 11/20 345/619 |
| 2007/0223800 A1 | 9/2007 | Guehring | |
| 2007/0226607 A1* | 9/2007 | Sakai | G11B 27/34 715/769 |
| 2008/0019580 A1 | 1/2008 | Ohyu et al. | |
| 2008/0034316 A1* | 2/2008 | Thoresson | G06F 3/04855 715/781 |
| 2008/0130979 A1 | 6/2008 | Ren et al. | |
| 2008/0183687 A1* | 7/2008 | Law | G06F 16/248 |
| 2008/0247618 A1* | 10/2008 | Laine | G06F 19/321 382/128 |
| 2008/0297513 A1 | 12/2008 | Greenhill et al. | |
| 2009/0037810 A1* | 2/2009 | Algreatly | G06T 7/11 715/247 |
| 2009/0043157 A1* | 2/2009 | Hirakawa | A61B 5/06 600/109 |
| 2009/0046898 A1* | 2/2009 | Li | G06Q 10/10 382/113 |
| 2009/0080744 A1* | 3/2009 | Sagawa | G06F 19/321 382/131 |
| 2009/0232378 A1* | 9/2009 | Nakamura | G06T 7/337 382/131 |
| 2010/0141654 A1* | 6/2010 | Neemuchwala | A61B 6/463 345/427 |
| 2011/0116701 A1 | 5/2011 | Zhu et al. | |
| 2011/0221866 A1* | 9/2011 | Ohta | G06F 1/1637 348/46 |
| 2012/0280922 A1* | 11/2012 | Lee | G06F 3/0485 345/173 |
| 2013/0094716 A1 | 4/2013 | Carpio et al. | |
| 2013/0094734 A1* | 4/2013 | Rauch | G06T 7/38 382/130 |
| 2013/0096414 A1 | 4/2013 | Lu et al. | |
| 2013/0117702 A1* | 5/2013 | Jang | G06F 15/0291 715/776 |
| 2013/0205247 A1* | 8/2013 | Erhard | G06F 3/016 715/781 |
| 2014/0037177 A1* | 2/2014 | Endo | G06T 11/00 382/131 |
| 2014/0105474 A1* | 4/2014 | Lee | G06T 7/0012 382/128 |
| 2014/0379703 A1* | 12/2014 | Martin | G06F 16/2455 707/723 |
| 2015/0023579 A1* | 1/2015 | Fujimoto | G16H 15/00 382/132 |
| 2015/0177977 A1* | 6/2015 | Amacker | G06F 3/04855 715/787 |
| 2015/0235365 A1* | 8/2015 | Mankovich | G06T 7/0014 382/131 |
| 2016/0071271 A1* | 3/2016 | Fujisawa | A61B 6/481 382/128 |
| 2017/0273641 A1* | 9/2017 | Haque | A61B 6/03 |

FOREIGN PATENT DOCUMENTS

| | | |
|---|---|---|
| JP | 2003150138 A | 5/2003 |
| JP | 2005160503 A | 6/2005 |
| JP | 2009-112531 A | 5/2009 |
| JP | 2009219655 A | 10/2009 |
| JP | 2012071122 A | 4/2012 |

* cited by examiner

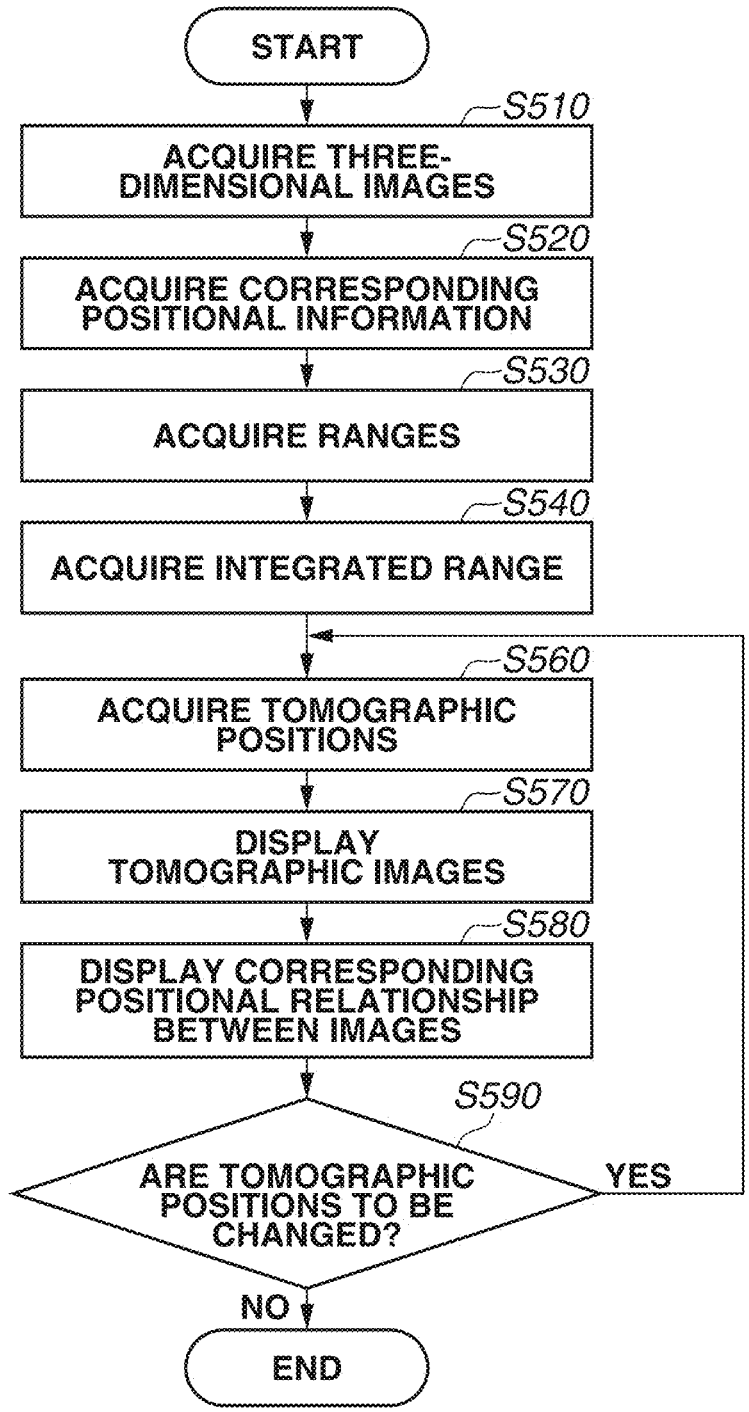

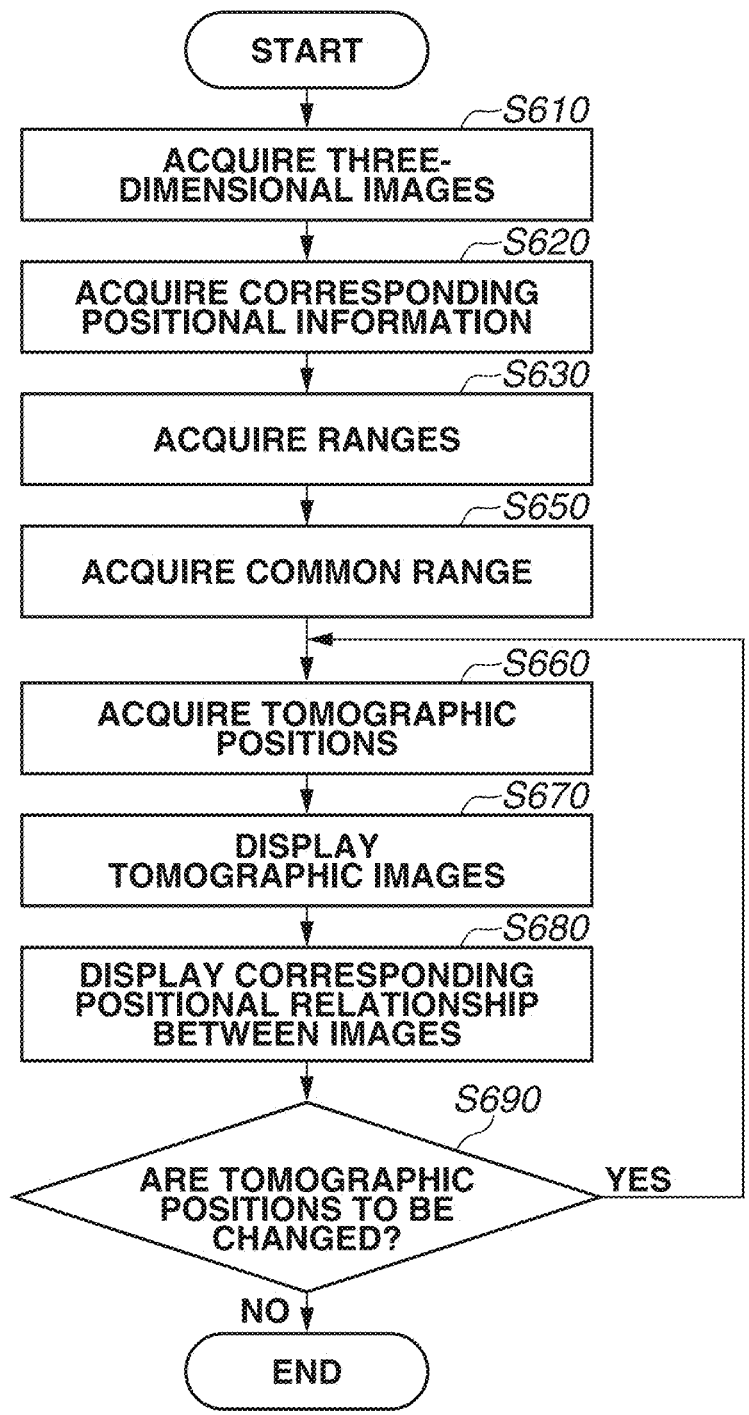

INFORMATION PROCESSING APPARATUS, SYSTEM, METHOD, AND STORAGE MEDIUM TO COMPARE IMAGES

BACKGROUND

Field of the Disclosure

The present disclosure generally relates to information processing and, more particularly, to an information processing apparatus, an information processing system, an information processing method, and a storage medium.

Description of the Related Art

When a doctor performs a medical examination using a medical image, the doctor sometimes observes a plurality of medical images while comparing the plurality of medical images to find a lesion or perform a follow-up examination. The publication of Japanese Patent Application Laid-Open No. 2009-112531 discusses a technique for limiting the range where cross-sectional images (two-dimensional images) included in volume data (a three-dimensional image) as a reference can be specified, to a range (a sum (union) area) including at least one of the range of the area where the volume data as the reference is reconfigured, and the range of the area where volume data as a comparison target is reconfigured.

SUMMARY

According to one or more aspects of the present disclosure, an information processing apparatus may include an acquisition unit configured to, based on information regarding positions of two-dimensional images included in a first three-dimensional image and two-dimensional images included in a second three-dimensional image different from the first three-dimensional image, acquire information regarding a first range, which is a range of positions where the two-dimensional images included in the first three-dimensional image are present, and a second range, which is different from the first range and is a range of positions where the two-dimensional images included in the second three-dimensional image are present, and a display control unit configured to display, on a display unit, a figure indicating the first range such that an area, in the first range, included in the second range is distinguishable.

Further features of the present disclosure will become apparent from the following description of exemplary embodiments with reference to the attached drawings.

BRIEF DESCRIPTION OF THE DRAWINGS

FIG. 5 is a flowchart illustrating an example of processing performed by an information processing apparatus according to a second exemplary embodiment.

FIG. 6 is a flowchart illustrating an example of processing performed by an information processing apparatus according to a third exemplary embodiment.

DESCRIPTION OF THE EMBODIMENTS

Exemplary embodiments of the present disclosure will be described below with reference to the drawings.

In the medical field, diagnostic imaging is performed by making a diagnosis based on a medical image obtained by an image capturing apparatus, such as an X-ray computed tomography (CT) apparatus and a magnetic resonance imaging (MRI) apparatus. A doctor performing diagnostic imaging makes a comprehensive determination, based on findings obtained from images and various measured values, to identify a lesion visualized in a medical image or the symptoms of a patient as a subject. In the diagnostic imaging, there is a case where a plurality of medical images obtained by different image capturing apparatuses are compared with each other, or a plurality of medical images captured at different times are compared with each other.

In a case where a user attempts to specify a cross-sectional image in a certain piece of volume data, and if the range where cross-sectional images in the piece of volume data can be specified is merely expanded to the sum area of the piece of volume data and another piece of volume data, the user may not be able to grasp the relative positional relationship between cross-sectional images in the respective pieces of volume data. An information processing apparatus 10 according to a first exemplary embodiment is directed to facilitating an operation for comparing a plurality of medical images.

Specifically, the information processing apparatus 10 can display a plurality of medical images such that tomographic positions corresponding to each other are in the same position in a positional relationship in a certain direction between the plurality of displayed medical images. The information processing apparatus 10 can display the range of positions overlapping each other in the certain direction between the plurality of medical images. Further, the information processing apparatus 10 can display scales or a series of marks indicating the positional relationship such that the scales are adjacent to the medical images. Consequently, a user observing the medical images can easily grasp the positional relationship between the plurality of medical images as observation targets. Further, the user can observe the medical images and grasp the positional relationship without largely moving the line of sight.

Figure 12:
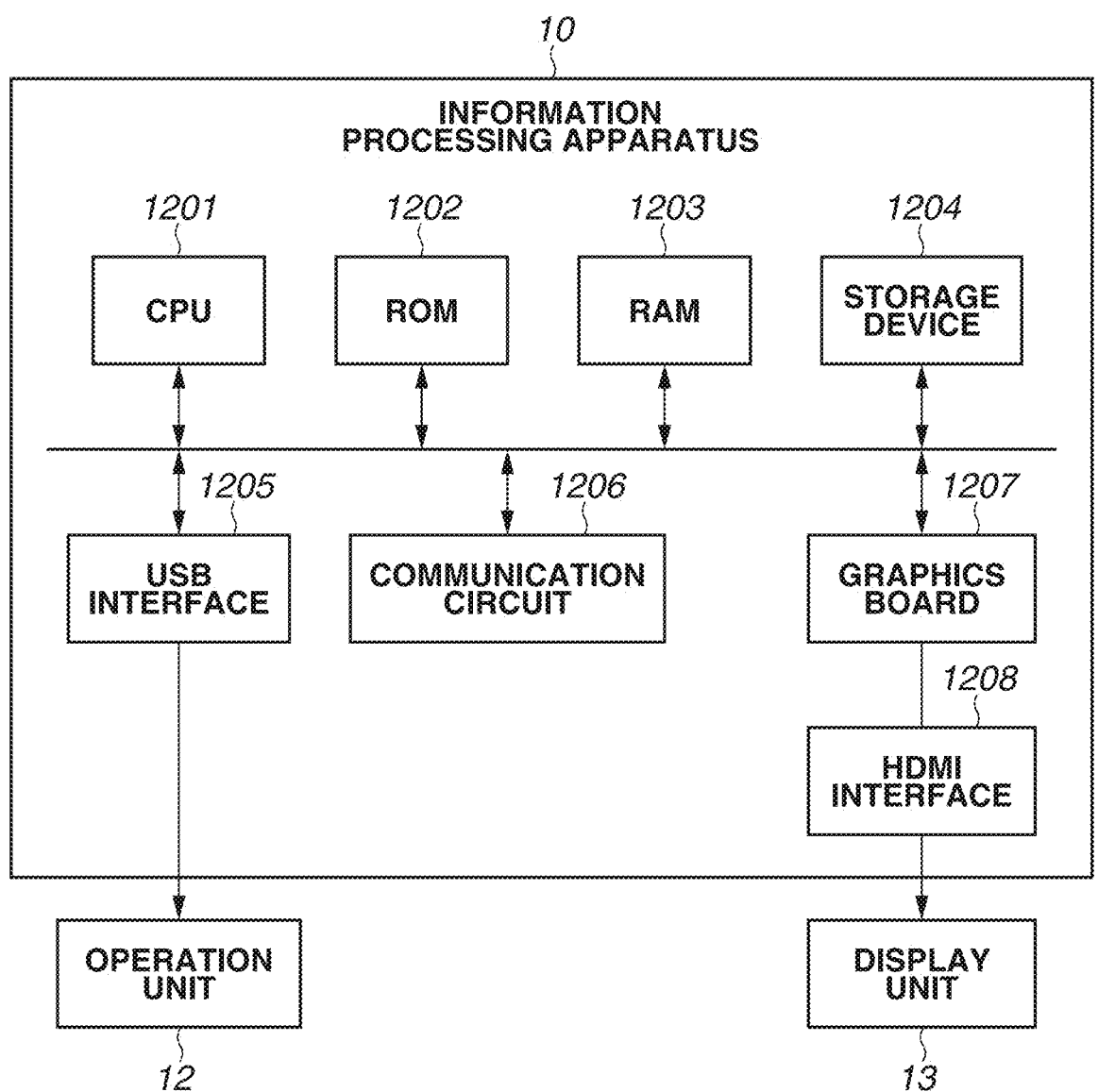
FIG. 12 is a diagram illustrating an example of a hardware configuration of an information processing apparatus according to one or more aspects of the present disclosure.

FIG. 12 is a diagram illustrating an example of the hardware configuration of the information processing apparatus 10 according to one or more aspects of the present disclosure. The information processing apparatus 10 is, for example, a computer. The information processing apparatus 10 includes a central processing unit (CPU) 1201, a read-only memory (ROM) 1202, a random-access memory (RAM) 1203, a storage device 1204, a Universal Serial Bus (USB) interface 1205, a communication circuit 1206, and a graphics board 1207. These components are connected together by a bus so that the components can communicate with each other. The bus is used to transmit and receive data between these pieces of hardware connected together, or transmit a command from the CPU 1201 to the other pieces of hardware.

The CPU 1201, which may include one or more processors and one or more memories, may be configured as a control circuit or circuitry for performing overall control of the information processing apparatus 10 and components connected to the information processing apparatus 10. The CPU 1201 executes a program stored in the ROM 1202 to perform control. Further, the CPU 1201 executes a display driver, which is software for controlling a display unit 13, to control the display of the display unit 13. Further, the CPU 1201 controls input and output to and from an operation unit 12.

The ROM 1202 stores a program in which the procedure for control by the CPU 1201 is stored, and data. The ROM 1202 stores a boot program for the information processing apparatus 10 and various types of initial data. Further, the ROM 1202 stores various programs for achieving the processing of the information processing apparatus 10.

The RAM 1203 provides a storage area for work when the CPU 1201 performs control according to a command program. The RAM 1203 includes a stack and a work area. The RAM 1203 stores a program for executing the processing of the information processing apparatus 10 and the components connected to the information processing apparatus 10, and various parameters for use in image processing. The RAM 1203 stores a control program to be executed by the CPU 1201 and temporarily stores various types of data to be used by the CPU 1201 to execute various types of control.

The storage device 1204 is an auxiliary storage device for saving various types of data such as an ultrasonic image and a photoacoustic image. The storage device 1204 is, for example, a hard disk drive (HDD) or a solid-state drive (SSD).

The USB interface 1205 is a connection unit for connecting to the operation unit 12.

The communication circuit 1206 is a circuit for communicating with components included in a system including the information processing apparatus 10, and with various external apparatuses connected to the information processing apparatus 10 via a network. For example, the communication circuit 1206 stores information to be output in a transfer packet and outputs the transfer packet to an external apparatus via the network by communication technology such as Transmission Control Protocol/Internet Protocol (TCP/IP). The information processing apparatus 10 may include a plurality of communication circuits according to a desired communication form.

The graphics board 1207 includes a graphics processing unit (GPU) and a video memory.

A High-Definition Multimedia Interface (HDMI) (registered trademark) interface 1208 is a connection unit for connecting to the display unit 13.

The CPU 1201 and the GPU are examples of a processor. Further, the ROM 1202, the RAM 1203, and the storage device 1204 are examples of a memory. The information processing apparatus 10 can include a plurality of processors and/or a plurality of memories. In the first exemplary embodiment, the functions of the components of the information processing apparatus 10 are achieved by the processor of the information processing apparatus 10 executing a program stored in the memory.

Further, the information processing apparatus 10 can include a CPU, a GPU, or an application-specific integrated circuit (ASIC) for exclusively performing a particular process. The information processing apparatus 10 can include a field-programmable gate array (FPGA) in which a particular process or all the processing is programmed.

Figure 1:
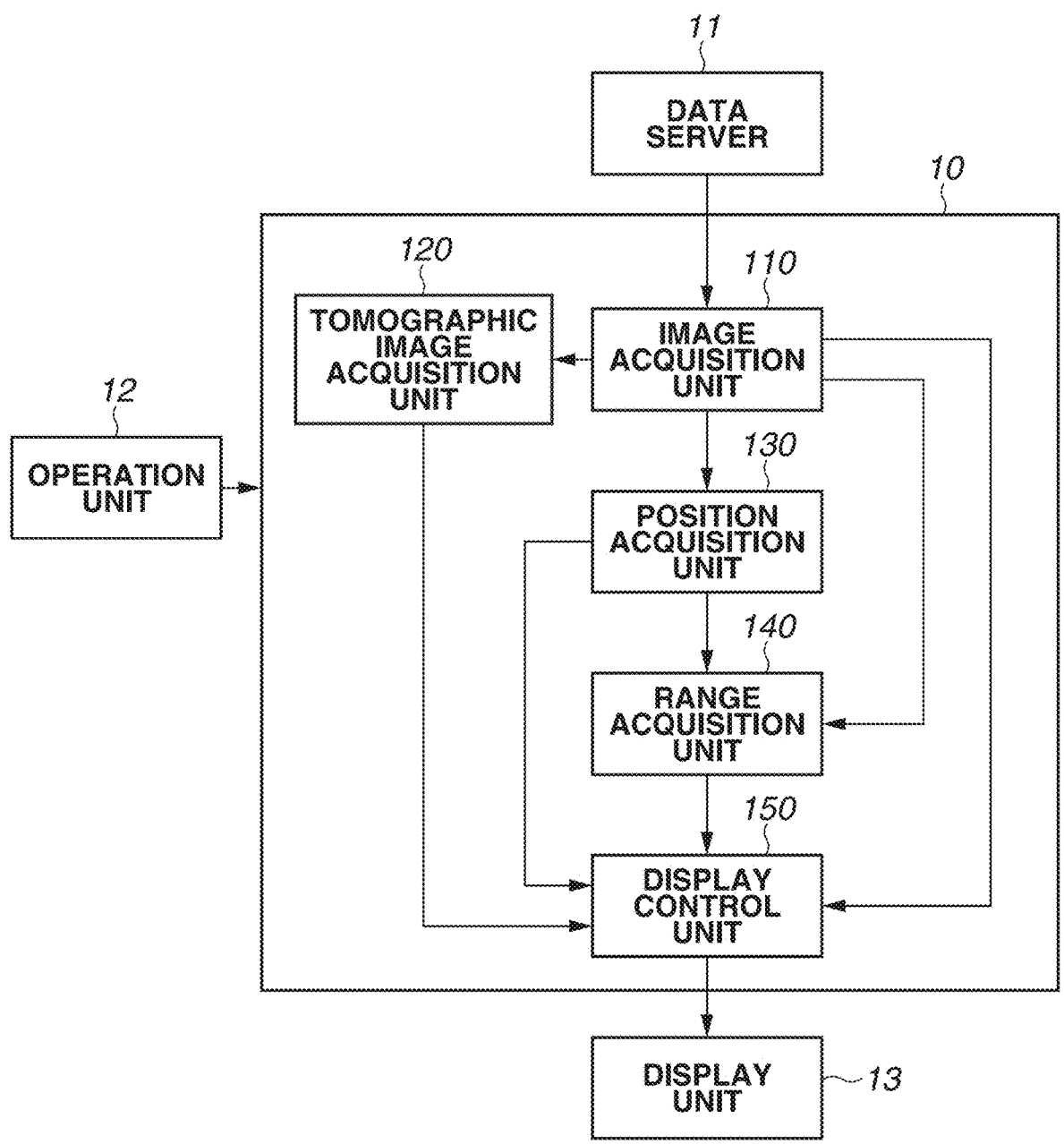
FIG. 1 is a diagram illustrating an example of a functional configuration of an information processing apparatus according to a first exemplary embodiment.

FIG. 1 is a diagram illustrating an example of the functional configuration of the information processing apparatus 10 according to the present exemplary embodiment. In the first exemplary embodiment, the information processing apparatus 10 is connected to a data server 11, the operation unit 12, and the display unit 13.

The data server 11 is a server for storing a medical image. The data server 11 is, for example, a picture archiving and communication system (PACS). In the first exemplary embodiment, the data server 11 holds a first three-dimensional image and a second three-dimensional image. The first and second three-dimensional images are, for example, three-dimensional images (volume data) captured by the same modality in different conditions (the date and time, a contrast condition, an imaging parameter, and the posture of a subject). In this case, the modality is any of, for example, an MRI apparatus, an X-ray CT apparatus, a three-dimensional ultrasonic image capturing apparatus, a photoacoustic tomography apparatus, a positron emission tomography (PET) apparatus, a single-photon emission computed tomography (SPECT) apparatus, and an optical coherence tomography (OCT) apparatus. For example, the first and second three-dimensional images can be images obtained by capturing the same subject in the same posture with the same modality at different dates and times for a follow-up examination. Alternatively, for example, the first and second three-dimensional images may be images obtained by capturing the same patient with different modalities or in different contrast conditions or with different imaging parameters. Yet alternatively, as another example, the first and second three-dimensional images may be images obtained by capturing different subjects, or may be an image of a subject and a standard image. The standard image is, for example, an image generated from average information (pixel values and part information) acquired from images of many patients. The first and second three-dimensional images are input to the information processing apparatus 10 via an image acquisition unit 110.

The operation unit 12 is, for example, a mouse and a keyboard. The user provides an operation input through the operation unit 12, and the information processing apparatus 10 receives information of the operation input.

The display unit 13 is, for example, a monitor. Based on the control of the information processing apparatus 10, a screen according to the first exemplary embodiment is displayed on the display unit 13.

The information processing apparatus 10 includes the image acquisition unit 110, a tomographic image acquisition unit 120, a position acquisition unit 130, a range acquisition unit 140, and a display control unit 150.

The image acquisition unit 110 acquires from the data server 11 the first and second three-dimensional images input to the information processing apparatus 10.

In the following descriptions, the image acquisition unit 110 uses a medical image compliant with Digital Imaging and Communications in Medicine (DICOM), which is a standard that defines the format of medical images and a communication protocol between apparatuses for handling the medical images. Hereinafter, data compliant with DICOM will occasionally be referred to as a "DICOM object". For example, a medical image as a DICOM object is composed of an area for recording image data and an area for recording metadata. The metadata includes an element identified by a tag. The area for recording metadata includes, for example, information regarding an image capturing apparatus having acquired the medical image, information regarding a subject (a patient), and information regarding an image capturing area. The information regarding an image capturing area is, for example, information for identifying an anatomical part of the subject from which the medical image is acquired. The information regarding an image capturing area can be represented by a numerical value, such as the distance from a particular anatomical structure, such as the clavicle, of the subject. A medical image can be an image not compliant with DICOM so long as information similar to that described in the following descriptions can be obtained from the medical image.

The tomographic image acquisition unit 120 acquires a first tomographic image included in the first three-dimensional image and a second tomographic image included in the second three-dimensional image. The first tomographic image is one of a plurality of two-dimensional images (tomographic images) included in the first three-dimensional image. The second tomographic image is one of a plurality of two-dimensional images (tomographic images) included in the second three-dimensional image.

The position acquisition unit 130 acquires corresponding positional information indicating the correspondence relationships between the positions where two-dimensional images included in the first three-dimensional image are present and the positions where two-dimensional images included in the second three-dimensional image are present. In another aspect, the corresponding positional information is information indicating the relative positions of two-dimensional images included in the second three-dimensional image to two-dimensional images included in the first three-dimensional image. In yet another aspect, the corresponding positional information is information indicating the amounts of shift in the positions of two-dimensional images included in the first three-dimensional image relative to the positions of two-dimensional images included in the second three-dimensional image. In yet another aspect, the corresponding positional information is information indicating the positions, in a subject, of two-dimensional images included in the first three-dimensional image, and the positions, in the subject, of two-dimensional images included in the second three-dimensional image.

The position acquisition unit 130 acquires, from information included in a three-dimensional image as a DICOM object, the positions where two-dimensional images included in the three-dimensional image are present. The position acquisition unit 130 acquires attribute information of the three-dimensional image. The attribute information is, for example, information indicating the characteristics of an element (a tag), which is a component of the DICOM object.

The attribute information in DICOM includes, for example, the following information. As information indicating the orientation of a subject (a patient), a patient orientation value or an image orientation (patient) value is included. As information indicating the position of the subject (the patient), an image position (patient) value or a slice location value is included. Based on the information indicating the orientation of the subject in the attribute information, information indicating the orientation of the subject visualized in each two-dimensional image is obtained. Further, based on the information indicating the position of the subject, information indicating the position of each two-dimensional image relative to a certain reference point of the subject, for example, in units of millimeters is obtained. That is, based on information regarding the directions, in a subject, of the two-dimensional images included in the three-dimensional image (the orientation of the subject), the position acquisition unit 130 acquires information regarding the range of the positions where the two-dimensional images included in the three-dimensional image are present.

Based on the corresponding positional information acquired by the position acquisition unit 130, the range acquisition unit 140 acquires a first range of the first three-dimensional image and a second range of the second three-dimensional image. As used herein, a "range" generally refers to the range of the positions where two-dimensional images included in a three-dimensional image are present in a predetermined reference coordinate system. Further, the range acquisition unit 140 acquires an integrated range, which includes the range of the sum of the first and second ranges, and a common range, which is the range of the product of the first and second ranges.

The display control unit 150 displays the first and second tomographic images on the display unit 13. Further, the display control unit 150 displays, on the display unit 13, figures indicating the first range, the second range, the positions of the displayed tomographic images, the integrated range, and the common range. The figures indicating the integrated range and the common range may be, for example, scales.

The units described throughout the present disclosure are exemplary and/or preferable modules for implementing processes described in the present disclosure. The term "unit", as used herein, may generally refer to firmware, software, hardware, or other component, such as circuitry or the like, or any combination thereof, that is used to effectuate a purpose. The modules can be hardware units (such as circuitry, firmware, a field programmable gate array, a digital signal processor, an application specific integrated circuit or the like) and/or software modules (such as a computer readable program or the like). The modules for implementing the various steps are not described exhaustively above. However, where there is a step of performing a certain process, there may be a corresponding functional module or unit (implemented by hardware and/or software) for implementing the same process. Technical solutions by all combinations of steps described and units corresponding to these steps are included in the present disclosure.

Figure 2:
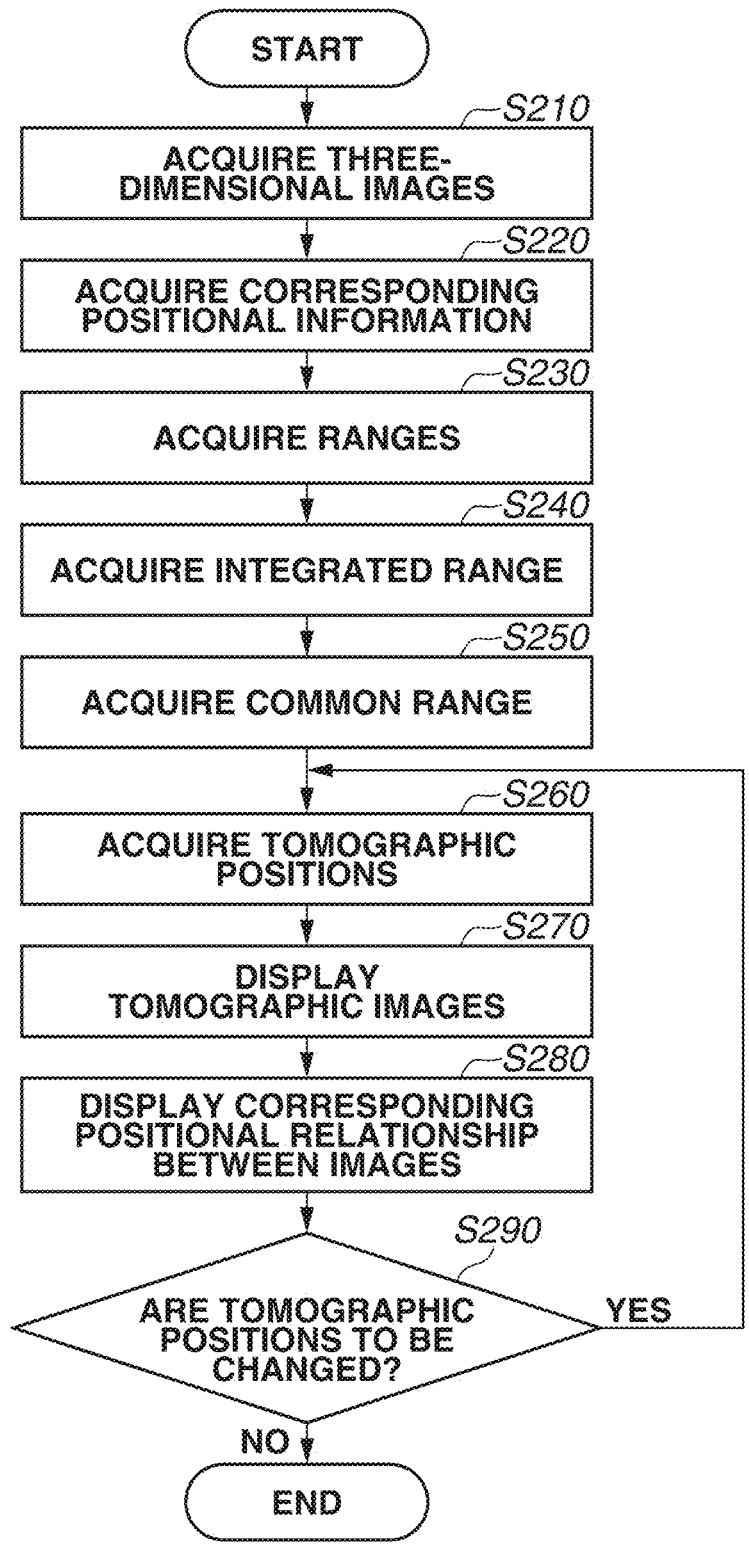
FIG. 2 is a flowchart illustrating an example of processing performed by the information processing apparatus according to the first exemplary embodiment.

FIG. 2 is a flowchart illustrating an example of the processing performed by the information processing apparatus 10.

(Step S210) (Acquire Three-Dimensional Images)

In step S210, the image acquisition unit 110 acquires a first three-dimensional image and a second three-dimensional image input to the information processing apparatus 10. Then, the image acquisition unit 110 outputs the acquired first and second three-dimensional images to the tomographic image acquisition unit 120, the position acquisition unit 130, the range acquisition unit 140, and the display control unit 150.

Figure 3:
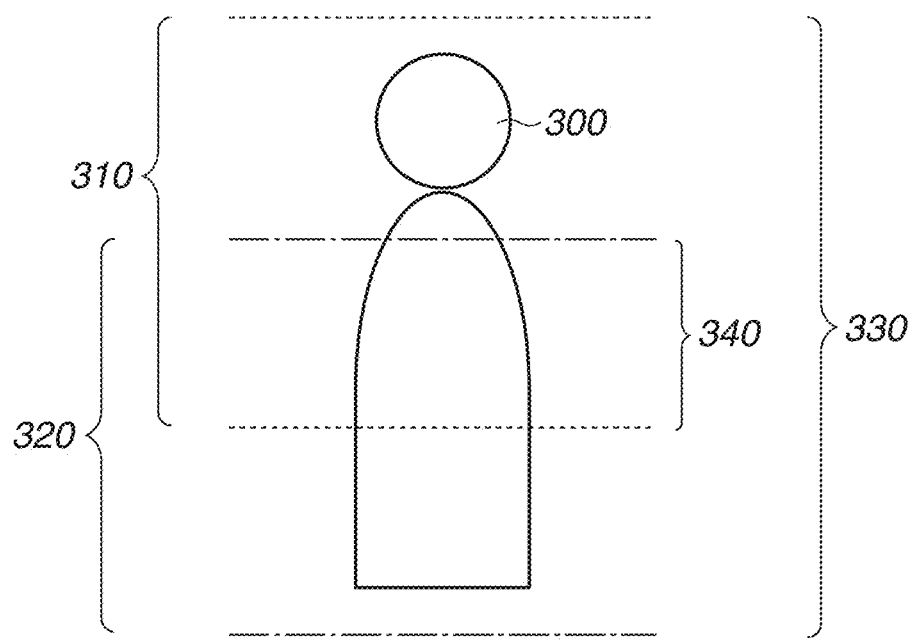
FIG. 3 is a diagram illustrating the processing performed by the information processing apparatus according to the first exemplary embodiment.

For example, as illustrated in FIG. 3, the image acquisition unit 110 acquires a first three-dimensional image composed of tomographic images in a range 310 from the head to the chest of a subject 300, and a second three-dimensional image composed of tomographic images in a range 320 from the chest to the abdomen of the same subject. The range 310 is an example of the first range, and the range 320 is an example of the second range.

(Step S220) (Acquire Corresponding Positional Information)

In step S220, the position acquisition unit 130 acquires corresponding positional information indicating the correspondence relationships between the positions of two-dimensional images (tomographic images) included in the first three-dimensional image acquired in step S210 and the positions of two-dimensional images (tomographic images) included in the second three-dimensional image also acquired in step S210. Then, the position acquisition unit 130 outputs the acquired corresponding positional information to the range acquisition unit 140 and the display control unit 150.

In this process, the position acquisition unit 130 can acquire the corresponding positional information by the operation unit 12 receiving an operation of the user on the mouse and the keyboard. For example, the user can select a single two-dimensional image (tomographic image) in each of the first and second three-dimensional images and specify that these two-dimensional images are at positions corresponding to each other (are tomographic images corresponding to each other) in a certain direction. Based on the correspondence relationship between the two-dimensional images specified based on the operation input provided by the user for the above specifying, the position acquisition unit 130 acquires corresponding positional information between the three-dimensional images. For example, the position acquisition unit 130 saves, as the corresponding positional information, information indicating that each tomographic image (S1_$i$) in the first three-dimensional image and each tomographic image (S2_$j$) in the second three-dimensional image are tomographic images corresponding to each other. Alternatively, when the tomographic positions, in the three-dimensional images, of the tomographic images S1_$i$ and S2_$j$ are P1_$i$ and P2_$j$, respectively, the position acquisition unit 130 acquires the offset (P1_$i$-P2_$j$) between the positions of the images and saves the value of the offset as the corresponding positional information.

Alternatively, the position acquisition unit 130 can acquire the corresponding positional information between the first and second three-dimensional images using apparatus coordinates representing the image capturing position of the subject on an image capturing apparatus. The apparatus coordinates can be acquired from, for example, header information of each of the three-dimensional images. Alternatively, when a three-dimensional image is captured, the position acquisition unit 130 can acquire, using an external apparatus, the position of a marker attached to the subject and set the position of the marker as the apparatus coordinates.

Alternatively, the position acquisition unit 130 can acquire the corresponding positional information by performing registration between the first and second three-dimensional images. The registration is, for example, image processing for deforming at least one of the first and second three-dimensional images so that pixels indicating the same position between the first and second three-dimensional images approximately coincide with each other. For example, the position acquisition unit 130 acquires the corresponding positional information by performing rigid registration between the images so that the degree of similarity between the images is high. In this case, the position acquisition unit 130 acquires, as the corresponding positional information, the amount of translation in a certain direction of conversion parameters for the positions and the orientations. As the degree of similarity between the images, the sum of squared difference (SSD), mutual information, or a cross-correlation coefficient can be used. Yet alternatively, the position acquisition unit 130 may compare the degrees of similarity in a histogram representing the distribution of pixel values between tomographic images included in the plurality of three-dimensional images and acquire, as the corresponding positional information, the amount of shift in a certain direction between tomographic images having the greatest degree of similarity.

In FIG. 3, based on the corresponding positional information, the positions of the ranges 310 and 320 are associated with each other so that the positions of tomographic images of the chest, which is a common part between the first and second three-dimensional images, coincide with each other.

(Step S230) (Acquire Ranges)

In step S230, the range acquisition unit 140 acquires the ranges (a first range and a second range) of the first and second three-dimensional images acquired in step S210. A description is given below using as an example a case where the range of transverse cross-sectional images included in each of the first and second three-dimensional images is acquired. First, the range acquisition unit 140 multiplies the number of pixels (the number of slices) in a craniocaudal direction, which is a direction orthogonal to the transverse cross-sectional images in each of the three-dimensional images, by a pixel size (slice thickness) in the craniocaudal direction, to acquire the widths (D1 and D2) in the craniocaudal direction of the three-dimensional images. Based on the widths in the craniocaudal direction of the three-dimensional images and the corresponding positional information acquired in step S220, the range acquisition unit 140 acquires the ranges of the respective three-dimensional images in a predetermined reference coordinate system. In this process, as the reference coordinate system, for example, a coordinate system in the craniocaudal direction in the images in the first three-dimensional image is used. The range acquisition unit 140 sets as the first range a range from 0, which is an upper end position of the first three-dimensional image (the position of the most cranial tomographic image in the craniocaudal direction), to D1, which is a lower end position of the first three-dimensional image (the position of the most caudal tomographic image, i.e., the tomographic image closest to the feet, in the craniocaudal direction). Further, based on the corresponding positional information acquired in step S220, the range acquisition unit 140 obtains an upper end position and a lower end position of the second three-dimensional image in the reference coordinate system and sets a range from the upper end position to the lower end position as the second range. The range acquisition unit 140 outputs the acquired first and second ranges to the display control unit 150. For example, in a case where the offset between the positions of the three-dimensional images is used as the corresponding positional information between the three-dimensional images, the first range is from 0 to D1, and the second range is from $(P1\_i-P2\_j)$ to $D2+(P1\_i-P2\_j)$.

In the above example, the second range is acquired using the first three-dimensional image as a reference. Alternatively, the first and second ranges can be acquired using the origin of the apparatus coordinates as a reference, or using any position determined by the user as a reference.

(Step S240) (Acquire Integrated Range)

In step S240, the range acquisition unit 140 acquires an integrated range, which is a range including the entirety of the first and second ranges. The range acquisition unit 140 outputs the acquired integrated range to the display control unit 150. The integrated range is an example of a third range, which is the range of the positions where two-dimensional images included in at least either of the first and second three-dimensional images are present.

In the example of FIG. 3, a range 330 from the upper end of the first range to the lower end of the second range is acquired as the integrated range.

(Step S250) (Acquire Common Range)

In step S250, the range acquisition unit 140 acquires a common range, which is the range of the product of the first and second ranges. The range acquisition unit 140 outputs the acquired common range to the display control unit 150. If an overlapping portion is not present between the two ranges, the range acquisition unit 140 outputs, to the display control unit 150, information indicating that the common range is "absent".

In the example of FIG. 3, a range 340 from the upper end of the second range to the lower end of the first range is acquired as the common range.

(Step S260) (Acquire Tomographic Positions)

In step S260, the tomographic image acquisition unit 120 acquires the positions of tomographic images to be displayed. In the above example, the tomographic image acquisition unit 120 acquires, as a first tomographic position, the position in the craniocaudal direction of the first three-dimensional image acquired in step S210. Similarly, the tomographic image acquisition unit 120 acquires the position in the craniocaudal direction of the second three-dimensional image as a second tomographic position. The tomographic image acquisition unit 120 outputs the acquired first and second tomographic positions to the display control unit 150.

The tomographic image acquisition unit 120 acquires the first and second tomographic positions by receiving an operation input provided by the user through the operation unit 12, such as the mouse and the keyboard. The tomographic positions specified by the user can be the positions of the ends or the centers of the respective ranges. Alternatively, the tomographic image acquisition unit 120 can acquire the first tomographic position and set the second tomographic position to the same position as the first tomographic position. Similarly, the tomographic image acquisition unit 120 can acquire the second tomographic position and set the first tomographic position to the same position as the second tomographic position. If an acquired tomographic position is outside the first range, the tomographic image acquisition unit 120 can set, as the first tomographic position, a position closest to the acquired tomographic position in a certain direction in the first range. Similarly, if an acquired tomographic position is outside the second range, the tomographic image acquisition unit 120 can set, as the second tomographic position, a position closest to the acquired tomographic position in a certain direction in the second range. (Step S270) (Display Tomographic Images)

In step S270, the display control unit 150 performs control to display, on the display unit 13, a first tomographic image at the first tomographic position of the first three-dimensional image and a second tomographic image at the second tomographic position of the second three-dimensional image.

As an example of the display of the tomographic images on the display unit 13, for example, the display control unit 150 can display the first and second tomographic images next to each other by dividing a single screen vertically or horizontally. As another example, the display control unit 150 can display, in a superimposed manner, the first tomographic image and the second tomographic image in a color different from that of the first tomographic image. As yet another example, the display control unit 150 can display only one of the first and second tomographic images. In this case, the display control unit 150 can display the first and second tomographic images at the same position by alternately switching the first and second tomographic images at predetermined time intervals. As yet another example, the display control unit 150 can display the first and second tomographic images by, according to the resolution of one of the images, enlarging or reducing the other image, or can display the first and second tomographic images next to each other such that the positions of the subject displayed in the first and second tomographic images correspond to each other.

If the first tomographic position is outside the first range, the display control unit 150 can display, for example, a screen in gray or another color without displaying a tomographic image. Alternatively, the display control unit 150 can display a tomographic image at a position closest to the first tomographic position in a certain direction in the first range. The same applies to the second tomographic position and the second range.

(Step S280) (Display Corresponding Positional Relationship between Images)

In step S280, the display control unit 150 displays, on the display unit 13, a figure indicating the first range at a relative position to the second range. Further, the display control unit 150 displays, on the display unit 13, a figure indicating the second range at a relative position to the first range. The display control unit 150 can display the figure indicating the first range on, or next to, a two-dimensional image in the first three-dimensional image. The display control unit 150 can display the figure indicating the second range on, or next to, a two-dimensional image in the second three-dimensional image.

Further, the display control unit 150 can display the figure indicating the first range together with a figure indicating the first tomographic position, and can display the figure indicating the first range next to a figure indicating the integrated range. Additionally, the display control unit 150 can display a figure indicating the common range next to the figure indicating the first range. Similarly, the display control unit 150 can display the figure indicating the second range together with a figure indicating the second tomographic position, or can display the figure indicating the second range next to a figure indicating the integrated range. Additionally, the display control unit 150 can display a figure indicating the common range next to the figure indicating the second range. If it is determined in step S250 that the common range is not present, the display control unit 150 can skip displaying the figures indicating the common range.

The process of step S250 is not essential, and the range acquisition unit 140 is not needed to acquire the common range. Further, the processes of steps S240 and S250 are not limited to the illustrated order. Further, a description has been given using as an example a case where transverse cross-sectional images in three-dimensional images are acquired as tomographic images. The present disclosure, however, is not limited to this. The tomographic images in the three-dimensional images may be coronal plane images, sagittal plane images, or images at any cross sections (so-called oblique images). In any case, the range acquisition unit 140 acquires ranges in a direction orthogonal to the tomographic images.

FIGS. 4A to 4D are examples of display indicating, in each of three-dimensional images, the range of the positions where two-dimensional images (tomographic images) are present, the position of a tomographic image (a tomographic position), an integrated range, and a common range.

Figure 4A:
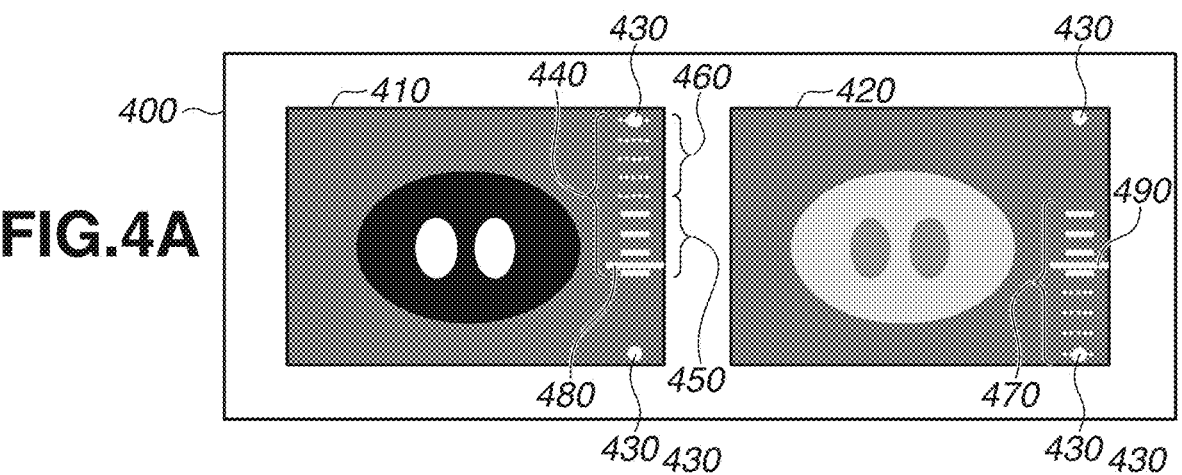
FIGS. 4A to 4D are diagrams illustrating examples of a screen displayed on a display unit by the information processing apparatus according to the first exemplary embodiment.

FIG. 4A is an example of a screen 400, which is displayed on the display unit 13. On the screen 400, a first tomographic image 410 and a second tomographic image 420 are displayed. Indicators 430, which are displayed in contact with the upper and lower ends of the first tomographic image 410 and the second tomographic image 420, indicate both ends of the integrated range. That is, the indicators 430 correspond to the positions of the upper and lower ends of the integrated range 330 illustrated in FIG. 3. A scale 440, which is composed of a solid line portion 450 and a dotted line portion 460, is an example of the figure indicating the first range and corresponds to the first range 310 illustrated in FIG. 3. Here, the scale 440, which corresponds to the first range, is displayed at a relative position to the second range. In another aspect, the scale 440, which corresponds to the first range, is displayed at a relative position to the integrated range (the third range). That is, the scale 440, which corresponds to the first range, is displayed with the same positional relationship as that between the first range 310 and the second range 320 or the integrated range 330 illustrated in FIG. 3. In this exemplary embodiment, the solid line portion 450 and the dotted line portion 460, which are included in the scale 440, indicate the position of each tomographic image (or each predetermined number of tomographic images). The intervals of the scale 440 are the intervals between the tomographic images (the intervals of resolution in a direction orthogonal to the tomographic images) or intervals specified in advance by the user. The intervals of the scale 440 can be changed according to the enlargement ratio of the tomographic image. The solid line portion 450 indicates the common range included in the first range. The dotted line portion 460 is an area that is included in the first range and does not overlap the second range. A scale 470 is an example of the figure indicating the second range and corresponds to the second range 320 illustrated in FIG. 3. A bar 480 indicates the first tomographic position. A bar 490 indicates the second tomographic position. The scale 440, which corresponds to the first range, and the scale 470, which corresponds to the second range, are displayed at relative positions to the second and first ranges. In the examples illustrated in FIGS. 4A to 4D, further, the scales are displayed by matching the integrated range to the width of each tomographic image. Thus, solid lines or dotted lines at the same tomographic position between the tomographic position included in the first range and the tomographic position included in the second range are displayed at the same position (level).

In the example of FIG. 4A, the ranges of the positions where two-dimensional images included in a plurality of three-dimensional images are present are displayed at relative positions to each other, whereby the user can grasp the tomographic positions in the respective three-dimensional images on the same basis. For example, the user matches the levels of the bars 480 and 490, which indicate the tomographic positions, and thus can display tomographic images at the same position (part) of the subject in the respective three-dimensional images on the display unit 13. Further, if the levels of the bars 480 and 490 are different from each other, the user can easily grasp how distant the first and second tomographic positions are from each other. Further, the user can grasp the relative positions of the first and second ranges by merely confirming the scale 440, which indicates the position of the first range in the integrated range. Further, the user can confirm the common range of the first and second ranges by merely confirming the solid line portion 450 of the scale 440. Then, according to the position where the bar 480, which indicates the first tomographic position, is present, the user can grasp whether a tomographic image at the same position in the subject as that of the second three-dimensional image is present at this tomographic position, or whether a tomographic image is present only in either one of the three-dimensional images at this tomographic position. Similar effects can also be obtained regarding the scale 470, which indicates the second range, and the bar 490, which indicates the second tomographic position.

Figure 4B:
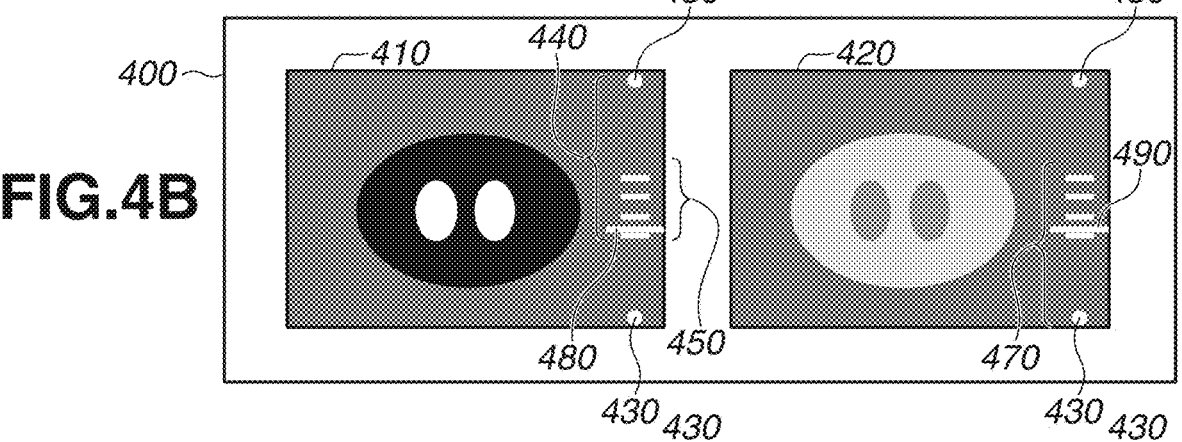
Figure 4C:
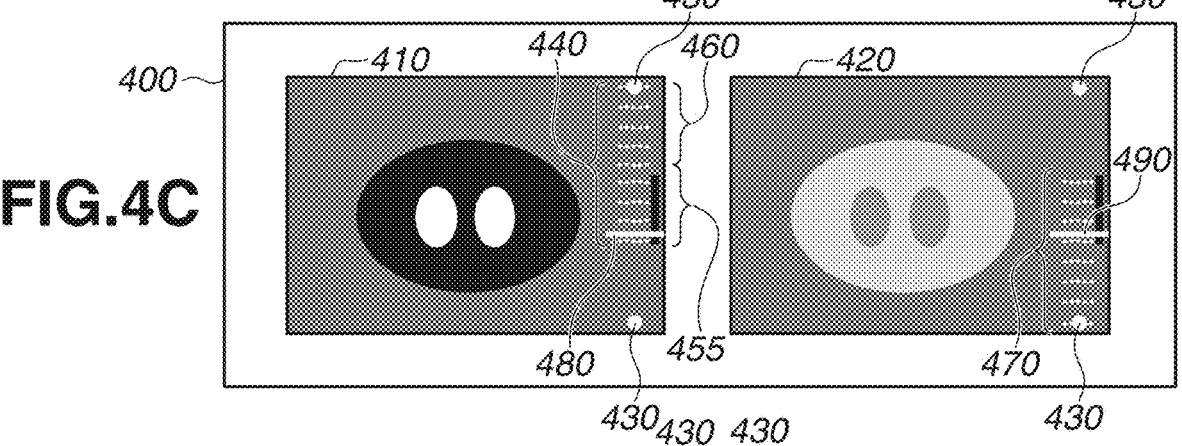

In the first exemplary embodiment, each of the figures indicating the first range, the first tomographic position, the integrated range, and the common range may be a scale, any figure, or a slider bar. In the first exemplary embodiment, the common range is indicated by a solid line portion, and another range is indicated by a dotted line portion. Alternatively, another form can be employed so long as the common range and another range can be distinguished from each other. The display control unit 150 can indicate each range by another shape, such as a dashed line or a chain line, or can indicate each range in a different color. Alternatively, as illustrated in FIG. 4B, the display control unit 150 can display only the figures indicating the common range. Yet alternatively, as illustrated in FIG. 4C, the display control unit 150 can display a figure (a scale) indicating each range and further display a figure in another form, such as a bar 455, as a figure indicating the common range.

Figure 4D:
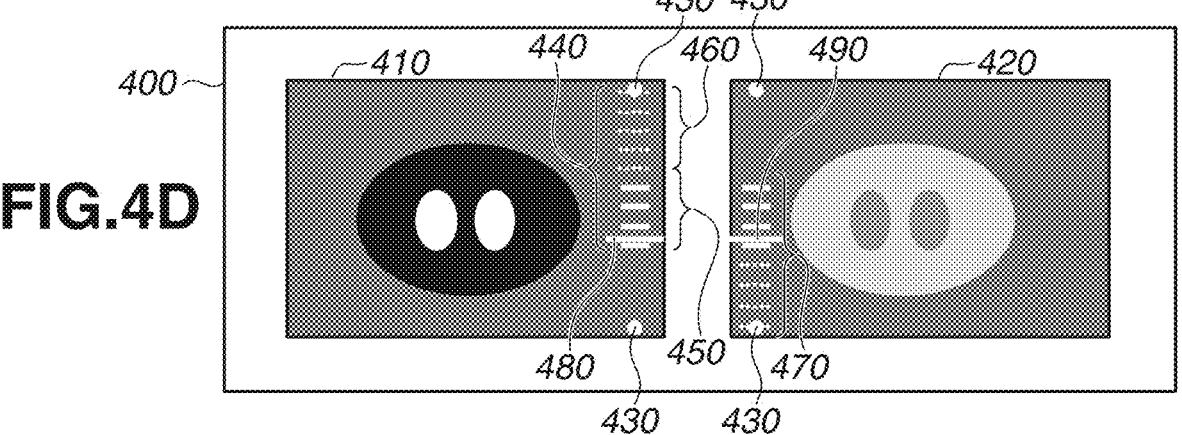

In FIG. 4A, the figures indicating the first range, the first tomographic position, and the common range are displayed between the indicators 430. Alternatively, the display control unit 150 can display these figures next to each other. Further, in a case where the integrated range is matched to the width of the tomographic image in the first three-dimensional image, the display control unit 150 is not needed to display the indicators 430. An example has been illustrated where the figures indicating the integrated range are displayed according to the vertical widths of the tomographic images. Alternatively, the display control unit 150 can display the figures indicating the integrated range in predetermined sizes, or display the figures indicating the integrated range according to the horizontal widths of the tomographic images, or display the figures indicating the integrated range in predetermined sizes in horizontal orientations or any orientations. The above various display forms are also applied to the display of the figure indicating the second range and the figure indicating the second tomographic position. The display control unit 150 can display the figures indicating the first range, the first tomographic position, the second range, and the second tomographic position next to each other. Further, in FIG. 4A, an example has been illustrated where the figures indicating the ranges and the positions of each tomographic image are displayed to the right of the tomographic image. Alternatively, as illustrated in FIG. 4D, to the left of some or all of the tomographic images, the display control unit 150 can display the figures indicating the ranges and the positions of the tomographic images. For example, the display control unit 150 can display the figure indicating the first range and the figure indicating the first tomographic position to the right of the first tomographic image, display the figure indicating the second range and the figure indicating the second tomographic position to the left of the second tomographic image, and display the first and second tomographic images next to each other in the left-right direction. Consequently, the figure indicating the first range and the figure indicating the second range are displayed at positions close to each other. Thus, the user can efficiently confirm the figures indicating the respective ranges without largely moving the line of sight.

(Step S290) (Are Tomographic Positions to Be Changed?)

In step S290, according to an operation input provided by the user through the operation unit 12, the processing of the tomographic image acquisition unit 120 branches. In a case where the operation input provided by the user is an instruction to change the tomographic positions (YES in step S290), the processing proceeds to step S260. In a case where the operation input provided by the user is an end instruction (NO in step S290), the processing illustrated in FIG. 2 ends.

Based on the above, figures indicating the ranges where two-dimensional images included in a plurality of three-dimensional images are present are displayed at relative positions to the respective ranges with respect to the plurality of three-dimensional images, whereby the user can easily grasp the tomographic positions of tomographic images displayed on a display unit, and the relative positional relationship between the tomographic images in a direction orthogonal to the tomographic images. In another aspect, a figure indicating a range of positions where two-dimensional images included in a certain three-dimensional image are present is displayed at a relative position to a range where two-dimensional images included in any of a plurality of three-dimensional images in the range of the positions are present, whereby the user can easily grasp the positional relationship between the two-dimensional images. Further, a common range of the ranges where two-dimensional images included in a plurality of three-dimensional images are present is displayed so that the common range can be distinguished by, for example, figures indicating the common range, whereby the user can grasp the common range between the plurality of three-dimensional images.

In the first exemplary embodiment, in step S280, the integrated range is explicitly displayed as the width between the indicators 430 in contact with the upper and lower ends of each tomographic image in FIGS. 4A to 4D. Alternatively, without displaying the integrated range, the display control unit 150 can display the width of a display object with a fixed width as the integrated range. For example, both ends of a scale display area determined in advance on a screen or the width of a currently displayed tomographic image can be both ends of a figure indicating the integrated range. Consequently, the corresponding positional relationship between images can be displayed without displaying the indicators 430 in FIGS. 4A to 4D. Thus, it is possible to obtain equivalent effects.

In the first exemplary embodiment, in step S230, the ranges of the images in a certain craniocaudal direction are acquired. Alternatively, in a case where the certain craniocaudal direction is a z-direction, the ranges of the images in an x-direction, a y-direction, or any direction can be acquired. Further, in step S270, tomographic images in the x-direction, the y-direction, or any direction can be displayed. For example, in a case where tomographic images orthogonal to the x-direction are displayed in step S270, then in step S280, an integrated range and a common range acquired from the ranges of the images in the x-direction, the ranges of the images, and the tomographic positions can be simultaneously displayed. Consequently, the user can efficiently observe and grasp tomographic images included in a plurality of three-dimensional images and the relative corresponding positional relationship between the images not only in a particular direction but also in any direction.

An information processing apparatus 10 according to a second exemplary embodiment displays, without acquiring a common range, figures indicating the ranges where two-dimensional images included in three-dimensional images are present, the positions of displayed tomographic images, and an integrated range, whereby the relative positional relationship in a certain direction between a plurality of three-dimensional images is presented to the user.

The hardware configuration of the information processing apparatus 10 according to the second exemplary embodiment is similar to that according to the exemplary embodiment illustrated in FIG. 12, and therefore, the detailed description of the hardware configuration is omitted here by incorporating the above description.

The functional configuration of the information processing apparatus 10 according to the second exemplary embodiment is similar to that according to the first exemplary embodiment illustrated in FIG. 1. Only components having functions different from those illustrated in the first exemplary embodiment are described below, and the detailed description of other components is omitted here by incorporating the above description.

The range acquisition unit 140 acquires a first range, a second range, and an integrated range of the first and second ranges. The display control unit 150 performs display control to display, on the display unit 13, a first tomographic image, a second tomographic image, a figure indicating the range of the position where each tomographic image included in respective three-dimensional images is present, a figure indicating the position of the displayed tomographic image, and a figure, such as scales indicating the integrated range.

FIG. 5 is a flowchart illustrating an example of the processing performed by the information processing apparatus 10. The processes of steps S510 to S540, S560, S570, and S590 are similar to those of steps S210 to S240, S260, S270, and S290, respectively, in the first exemplary embodiment, and therefore, the detailed description of these processes is omitted here by incorporating the above description.

(Step S580) (Display Corresponding Positional Relationship between Images)

In step S580, the display control unit 150 displays, on the display unit 13, a figure indicating the first range at a relative position to the second range. Further, the display control unit 150 displays, on the display unit 13, a figure indicating the second range at a relative position to the first range. The display control unit 150 can display the figure indicating the first range on, or next to, a two-dimensional image in the first three-dimensional image. The display control unit 150 can display the figure indicating the second range on, or next to, a two-dimensional image in the second three-dimensional image. Further, the display control unit 150 can display the figure indicating the first range together with a figure indicating the first tomographic position, and can display the figure indicating the first range next to a figure indicating the integrated range. The same applies to the second tomographic image, the figure indicating the second range, and a figure indicating the second tomographic position.

Based on the above, figures indicating the ranges where two-dimensional images included in a plurality of three-dimensional images are present are displayed at relative positions to the respective ranges with respect to the plurality of three-dimensional images, whereby the user can easily grasp the tomographic positions of tomographic images displayed on a display unit, and the relative positional relationship between the tomographic images in a direction orthogonal to the tomographic images. In another aspect, a figure indicating a range of positions where two-dimensional images included in a certain three-dimensional image are present is displayed at a relative position to a range where two-dimensional images included in any of a plurality of three-dimensional images in the range of the positions are present, whereby the user can easily grasp the positional relationship between the two-dimensional images.

An information processing apparatus 10 according to a third exemplary embodiment displays, without acquiring an integrated range, figures indicating the ranges where two-dimensional images included in three-dimensional images are present, the positions of displayed tomographic images, and a common range, whereby the relative positional relationship in a certain direction between a plurality of three-dimensional images is presented to the user.

The hardware configuration of the information processing apparatus 10 according to the third exemplary embodiment is similar to that according to the exemplary embodiment illustrated in FIG. 12, and therefore, the detailed description of the hardware configuration is omitted here by incorporating the above description.

The functional configuration of the information processing apparatus 10 according to the third exemplary embodiment is similar to that according to the first exemplary embodiment illustrated in FIG. 1. Only components having functions different from those illustrated in the first exemplary embodiment are described below, and the detailed description of other components is omitted here by incorporating the above description.

The range acquisition unit 140 acquires a first range, a second range, and a common range of the first and second ranges. The display control unit 150 performs display control to display, on the display unit 13, a first tomographic image, a second tomographic image, figures indicating the ranges of the positions where tomographic images included in three-dimensional images are present, figures indicating the positions of the displayed tomographic images, and figures such as scales indicating the common range.

FIG. 6 is a flowchart illustrating an example of the processing performed by the information processing apparatus 10. The processes of steps S610 to S630, S650, S670, and S690 are similar to those of steps S210 to S230, S250, S270, and S290, respectively, in the first exemplary embodiment, and therefore, the detailed description of these processes is omitted here by incorporating the above description.

(Step S680) (Display Corresponding Positional Relationship between Images)

The display control unit 150 displays, on the display unit 13, a figure indicating the first range at a relative position to the second range. Further, the display control unit 150 can display, on the display unit 13, a figure indicating the second range at a relative position to the first range. The display control unit 150 can display the figure indicating the first range on, or next to, a two-dimensional image in the first three-dimensional image. The display control unit 150 can display the figure indicating the second range on, or next to, a two-dimensional image in the second three-dimensional image. Further, the display control unit 150 can display a figure indicating the common range next to the figure indicating the first range.

Figure 7:
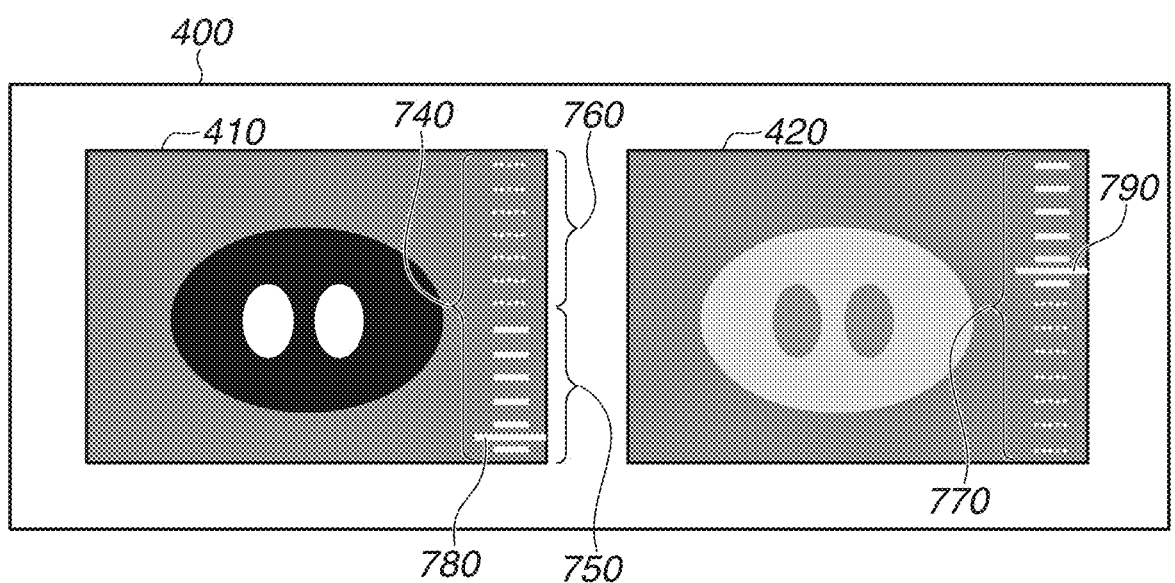
FIG. 7 is a diagram illustrating an example of a screen displayed on a display unit by the information processing apparatus according to the third exemplary embodiment.

FIG. 7 is an example of display indicating, in each of three-dimensional images, the range of the positions where tomographic images are present, a tomographic position, and a common range. Components similar to those in the examples illustrated in FIGS. 4A to 4D are designated by the same numerals, and the detailed description of these components is omitted here by incorporating the above description.

A scale 740 is a figure indicating the first range. A solid line portion 750 indicates the common range. A dotted line portion 760 indicates the range where the positions of tomographic images included in the second range are not present in the first range. A scale 770 is a figure indicating the second range. A bar 780 and a bar 790 indicate the first tomographic position and the second tomographic position, respectively. Consequently, the user can easily confirm a common range of the positions where two-dimensional images included in a plurality of three-dimensional images are present.

The figures indicating the first range, the first tomographic position, and the common range can be displayed next to each other, and can be further displayed next to the figures indicating the second range and the second tomographic position. Alternatively, the display control unit 150 can display the figures indicating the common range and the figures indicating the first and second tomographic positions without displaying the figures indicating the first and second ranges.

Based on the above, the user can easily grasp the relative positional relationship between two-dimensional images included in a plurality of three-dimensional images. Further, a figure indicating each range is displayed by, for example, matching both ends of the figure to the width of a tomographic image, whereby, even if the range where the figure can be displayed is small, it is possible to present the relative positional relationship to the user.

An information processing apparatus 10 according to a fourth exemplary embodiment acquires, as an integrated range, a range determined in advance in order to include a first range and a second range, and displays the first and second ranges in the integrated range, whereby the relative positional relationship in a certain direction between tomographic images in a plurality of three-dimensional images is presented to the user.

The hardware configuration of the information processing apparatus 10 according to the fourth exemplary embodiment is similar to that according to the exemplary embodiment illustrated in FIG. 12, and therefore, the detailed description of the hardware configuration is omitted here by incorporating the above description.

The functional configuration of the information processing apparatus 10 according to the fourth exemplary embodiment is similar to that according to the first exemplary embodiment illustrated in FIG. 1. Only components having functions different from those illustrated in the first exemplary embodiment are described below, and the detailed description of other components is omitted here by incorporating the above description.

The range acquisition unit 140 acquires, as an integrated range, a range including both a first range and a second range.

Figure 8:
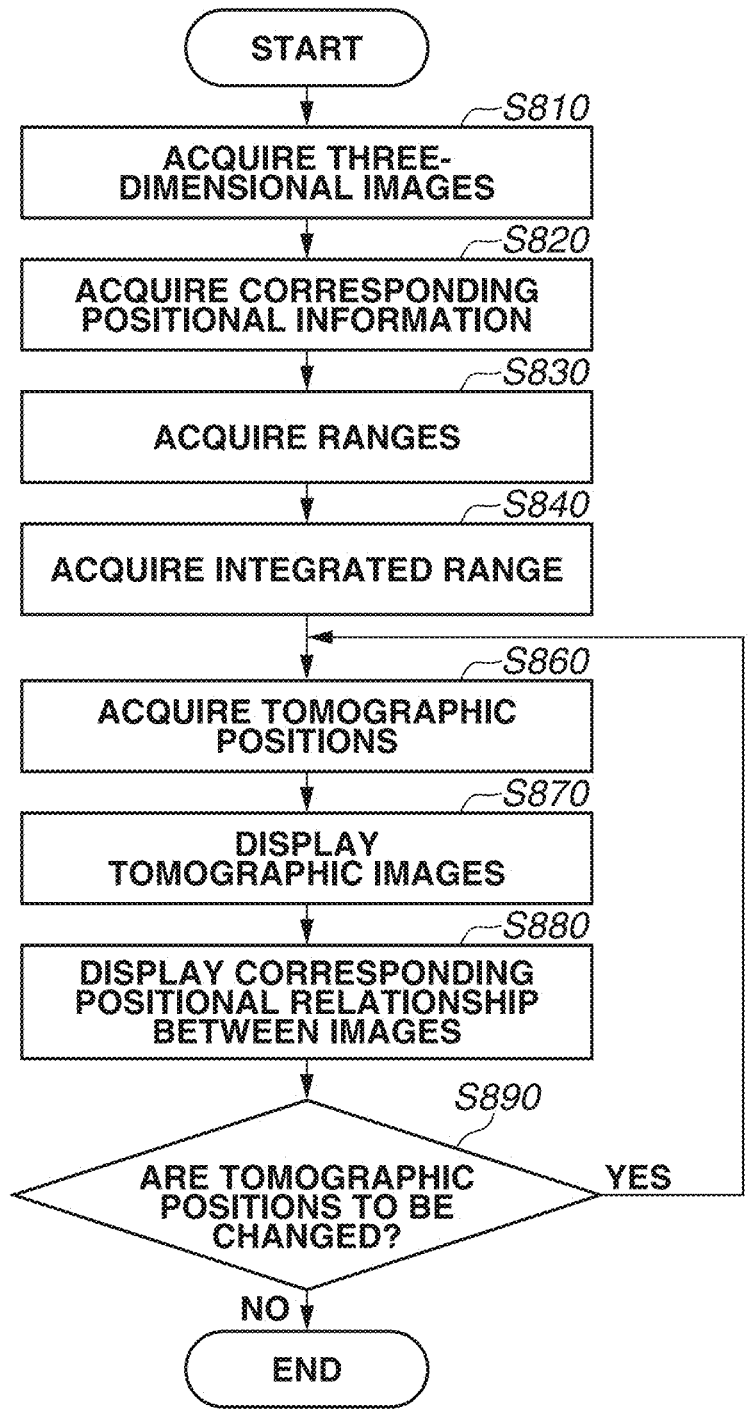
FIG. 8 is a flowchart illustrating an example of processing performed by an information processing apparatus according to a fourth exemplary embodiment.

FIG. 8 is a flowchart illustrating an example of the processing performed by the information processing apparatus 10. The processes of steps S810, S820, S860, S870, and S890 are similar to those of steps S210, S220, S260, S270, and S290, respectively, in the first exemplary embodiment, and therefore, the detailed description of these processes is omitted here by incorporating the above description.

(Step S830) (Acquire Ranges)

In step S830, the range acquisition unit 140 acquires a first range and a second range. In the fourth exemplary embodiment, using an apparatus coordinate system as a reference coordinate system, the range acquisition unit 140 acquires the first and second ranges in the reference coordinate system. The rest of the processing is similar to that in step S230, and therefore is not described here. The apparatus coordinate system can be acquired from, for example, header information of the first or second three-dimensional image.

(Step S840) (Acquire Integrated Range)

In step S840, based on the apparatus coordinate system acquired in step S830, the range acquisition unit 140 acquires an integrated range. Then, the range acquisition unit 140 outputs the acquired integrated range to the display control unit 150.

In the fourth exemplary embodiment, in order for the integrated range to include the first and second ranges, the range acquisition unit 140 sets as the integrated range, for example, a range that can be captured by an image capturing apparatus having captured three-dimensional images as display targets. Consequently, the integrated range can include, for example, both the ranges of a first three-dimensional image obtained by capturing the head to the chest, and a second three-dimensional image obtained by capturing the chest to the abdomen. As an example of the integrated range, the entire range of possible values of the apparatus coordinates determined based on the range that can be captured by the image capturing apparatus can be used.

(Step S880) (Display Corresponding Positional Relationship between Images)

In step S880, the display control unit 150 displays, on the display unit 13, a figure indicating the first range at a relative position to the second range. Further, the display control unit 150 can display, on the display unit 13, a figure indicating the second range at a relative position to the first range. The display control unit 150 can display the figure indicating the first range on, or next to, a two-dimensional image in the first three-dimensional image. The display control unit 150 can display the figure indicating the second range on, or next to, a two-dimensional image in the second three-dimensional image. Further, the display control unit 150 can display the figure indicating the first range together with a figure indicating the first tomographic position, and can display the figure indicating the first range next to a figure indicating the integrated range. The same applies to the second tomographic image, the figure indicating the second range, and a figure indicating the second tomographic position.

Based on the above, the user can easily grasp the relative positional relationship between two-dimensional images included in a plurality of three-dimensional images. Particularly, based on an integrated range determined in advance in order to include both a first range and a second range, the first and second ranges are displayed, whereby the user can efficiently grasp the relative positional relationship between the first and second ranges. Further, regardless of the combination of input three-dimensional images, it is possible to display, at uniform positions, uniform scales indicating the positions where two-dimensional images included in the three-dimensional images are present. Thus, even in a case where another three-dimensional image is input instead of or in addition to a second three-dimensional image, the display form of a scale indicating the first range does not change. The user can observe a plurality of medical images without being conscious of changes in the positions or the intervals of scales due to the combination of input images.

In a fifth exemplary embodiment, an example is described where the relative positional relationships between the ranges of the positions where two-dimensional images included in three or more three-dimensional images are present are displayed.

The hardware configuration of an information processing apparatus 10 according to the fifth exemplary embodiment is similar to that according to the exemplary embodiment illustrated in FIG. 12, and therefore, the detailed description of the hardware configuration is omitted here by incorporating the above description.

The functional configuration of the information processing apparatus 10 according to the fifth exemplary embodiment is similar to that according to the first exemplary embodiment illustrated in FIG. 1. Only components having functions different from those illustrated in the first exemplary embodiment are described below, and the detailed description of other components is omitted here by incorporating the above description.

The image acquisition unit 110 acquires three or more three-dimensional images, such as a first three-dimensional image, a second three-dimensional image, and a third three-dimensional image, input to the information processing apparatus 10. The tomographic image acquisition unit 120 acquires a first tomographic image, a second tomographic image, and a third tomographic image, which is one of tomographic images included in the third three-dimensional image.

The position acquisition unit 130 acquires corresponding positional information indicating the correspondence relationships between the positions where two-dimensional images included in the first three-dimensional image are present, the positions where two-dimensional images included in the second three-dimensional image are present, and the positions where two-dimensional images included in the third three-dimensional image are present.

Based on the corresponding positional information, the range acquisition unit 140 acquires a first range, a second range, the range of the positions where the two-dimensional images included in the third three-dimensional image are present, and an integrated range of these three ranges. Further, the range acquisition unit 140 acquires common ranges of the respective combinations of these three ranges.

The display control unit 150 displays tomographic images in the first, second, and third three-dimensional images on the display unit 13. Further, the display control unit 150 displays, on the display unit 13, figures indicating the first range, the second range, and the range of the positions where the two-dimensional images included in the third three-dimensional image are present. Further, the display control unit 150 displays, on the display unit 13, figures indicating the integrated range and the common ranges.

Figure 9:
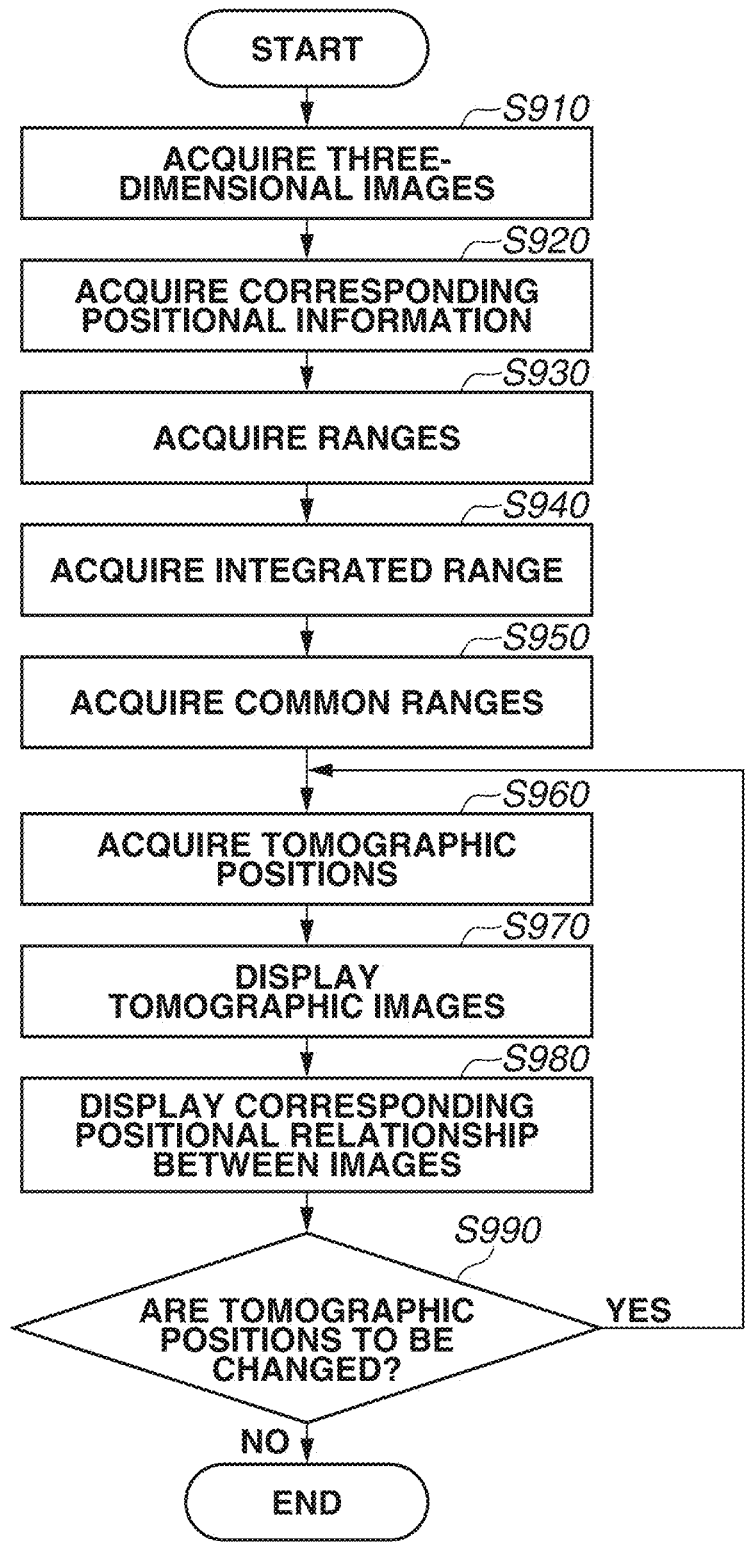
FIG. 9 is a flowchart illustrating an example of processing performed by an information processing apparatus according to a fifth exemplary embodiment.

FIG. 9 is a flowchart illustrating an example of the processing performed by the information processing apparatus 10. The process of step S990 is similar to that of step S290 in the first exemplary embodiment, and therefore, the detailed description of this process is omitted here by incorporating the above description.

(Step S910) (Acquire Three-Dimensional Images)

In step S910, the image acquisition unit 110 acquires a first three-dimensional image, a second three-dimensional image, and a third three-dimensional image input to the information processing apparatus 10. Then, the image acquisition unit 110 outputs the acquired first, second, and third three-dimensional images to the tomographic image acquisition unit 120, the position acquisition unit 130, and the display control unit 150.

(Step S920) (Acquire Corresponding Positional Information)

In step S920, the position acquisition unit 130 acquires corresponding positional information of the plurality of three-dimensional images acquired in step S910. Then, the position acquisition unit 130 outputs the acquired corresponding positional information to the range acquisition unit 140 and the display control unit 150.

In the fifth exemplary embodiment, the position acquisition unit 130 acquires corresponding positional information regarding all the combinations of the plurality of three-dimensional images acquired in step S910. As another example, the position acquisition unit 130 can acquire corresponding positional information between the first and second three-dimensional images and corresponding positional information between the first and third three-dimensional images. Then, from these pieces of corresponding positional information, the position acquisition unit 130 can acquire corresponding positional information between the second and third three-dimensional images.

(Step S930) (Acquire Ranges)

In step S930, based on the corresponding positional information acquired in step S920, the range acquisition unit 140 acquires a first range, a second range, and the range of the positions where two-dimensional images included in the third three-dimensional image are present. Then, the range acquisition unit 140 outputs information regarding the acquired ranges to the display control unit 150.

(Step S940) (Acquire Integrated Range)

In step S940, the range acquisition unit 140 acquires an integrated range, which is a range including the entirety of the first range, the second range, and the range of the positions where the two-dimensional images included in the third three-dimensional image are present. The range acquisition unit 140 outputs the acquired integrated range to the display control unit 150.

(Step S950) (Acquire Common Ranges)

In step S950, based on the corresponding positional information acquired in step S920, the range acquisition unit 140 acquires common ranges, which are the ranges of the products of the respective combinations (six combinations) of the first range, the second range, and the range of the positions where the two-dimensional images included in the third three-dimensional image are present. The range acquisition unit 140 outputs the acquired common ranges to the display control unit 150. If an overlapping portion is not present in any of the combinations, the range acquisition unit 140 outputs, to the display control unit 150, information indicating that the common range is "absent" in this combination.

(Step S960) (Acquire Tomographic Positions)

In step S960, the tomographic image acquisition unit 120 acquires the positions of tomographic images to be displayed. Here, the tomographic image acquisition unit 120 acquires, as a first tomographic position, the position in the craniocaudal direction of the first three-dimensional image acquired in step S910. Similarly, the tomographic image acquisition unit 120 acquires the position in the craniocaudal direction of the second three-dimensional image as a second tomographic position and acquires the position in the craniocaudal direction of the third three-dimensional image as a third tomographic position. The tomographic image acquisition unit 120 outputs the acquired first, second, and third tomographic positions to the display control unit 150.

(Step S970) (Display Tomographic Images)

In step S970, the display control unit 150 performs control to display on the display unit 13 a first tomographic image at the first tomographic position of the first three-dimensional image, a second tomographic image at the second tomographic position of the second three-dimensional image, and a third tomographic image at the third tomographic position of the third three-dimensional image.

The display control unit 150 can perform display, similarly to the first exemplary embodiment, according to an operation input provided by the user to specify two of the tomographic images acquired in step S960, or can simultaneously display three or more tomographic images.

(Step S980) (Display Corresponding Positional Relationship between Images)

In step S980, the display control unit 150 displays, on the display unit 13, a figure indicating the first range at a relative position to the second range and the range of the positions where the two-dimensional images included in the third three-dimensional image are present. Further, the display control unit 150 displays, on the display unit 13, a figure indicating the second range at a relative position to the first range and the range of the positions where the two-dimensional images included in the third three-dimensional image are present. Further, the display control unit 150 can display, on the display unit 13, at a relative position to the first and second ranges, a figure indicating the range of the positions where the two-dimensional images included in the third three-dimensional image are present. Other examples of display are similar to those in step S280 in the first exemplary embodiment, and therefore, the detailed description of the other examples is omitted here by incorporating the above description.

Figure 10:
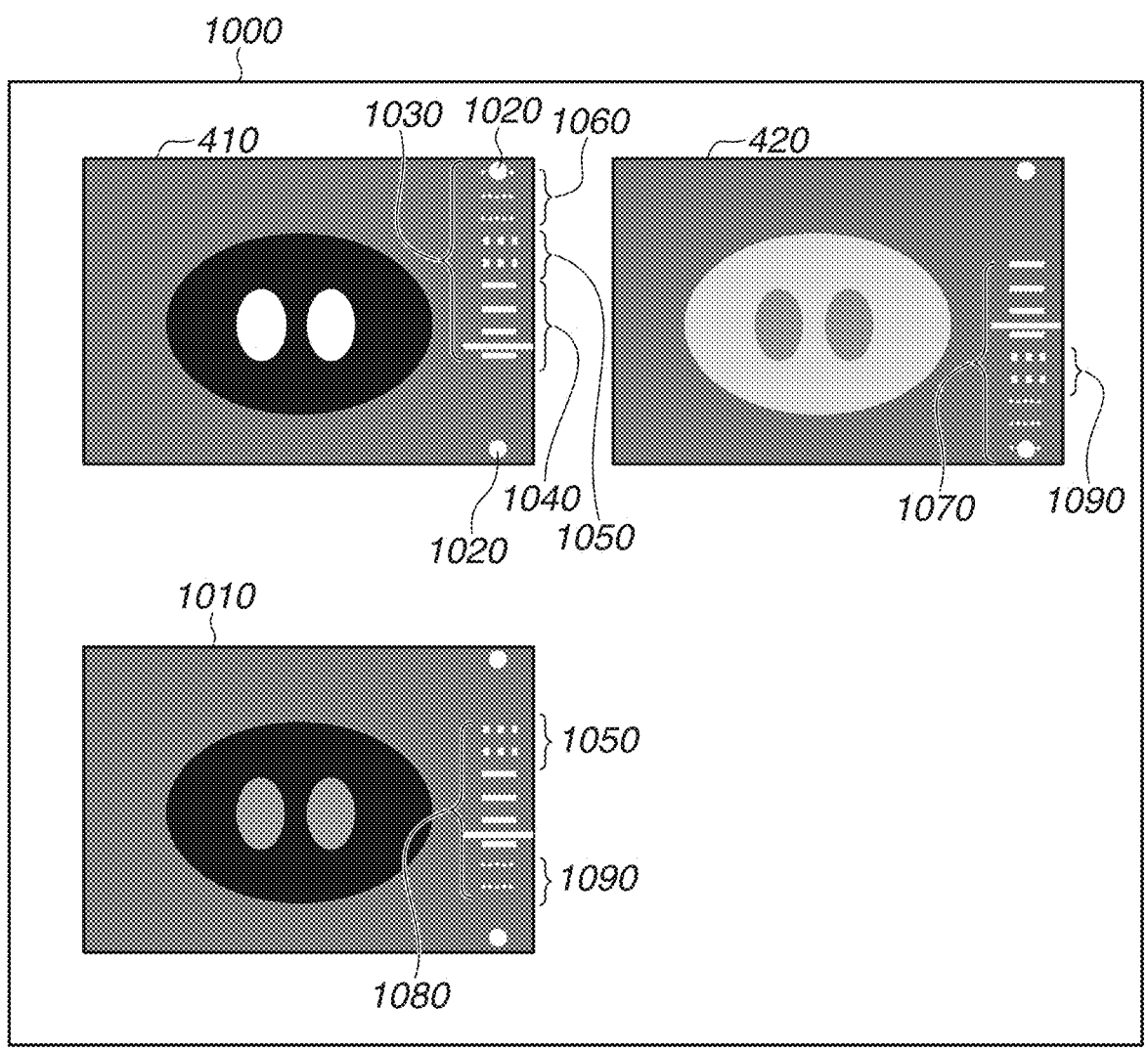
FIG. 10 is a diagram illustrating an example of a screen displayed on a display unit by the information processing apparatus according to the fifth exemplary embodiment.

FIG. 10 is an example of display indicating, in each of three-dimensional images, the range of the positions where two-dimensional images (tomographic images) are present, the position of a tomographic image (a tomographic position), an integrated range, and common ranges. In the example illustrated in FIG. 10, a third tomographic image 1010 is displayed in addition to the first tomographic image 410 and the second tomographic image 420 illustrated in FIG. 4A. The range between indicators 1020 indicates the integrated range. Scales 1030, 1070, and 1080 indicate the first range, the second range, and the range of the positions where the two-dimensional images included in the third three-dimensional image are present, respectively. Ranges 1040 indicate the common ranges of the three three-dimensional images. Ranges 1050 indicate the common range of the first range and the range of the positions where the two-dimensional images included in the third three-dimensional image are present. Ranges 1090 indicate the common range of the second range and the range of the positions where the two-dimensional images included in the third three-dimensional image are present. As described above, the display control unit 150 displays figures (e.g., scales) indicating ranges by changing the display forms of the figures according to the combinations and the number of three-dimensional images in which tomographic positions corresponding to each other are present between a plurality of three-dimensional images (in other words, according to the degrees of overlap in range between the plurality of three-dimensional images). Consequently, the user simply views figures, such as scales, indicating respective ranges and thereby can easily grasp the number and the combinations of tomographic images present at tomographic positions in the respective ranges. Further, the user compares the display forms of figures at the same position and thereby can easily confirm between which three-dimensional images tomographic images corresponding to each other are present.

In the above example, common ranges of all the combinations of the three-dimensional images acquired in step S910 are acquired. Alternatively, the combination of three-dimensional images of which a common range is to be acquired, or the combination of three-dimensional images of which a common range is to be displayed can be limited. For example, the combination of three-dimensional images of which a common range is to be displayed can be limited to a pair of three-dimensional images between which the comparison is important. The user can define the degree of importance of each combination of images in advance and make a setting so that a common range of only a pair of images satisfying a predetermined condition (e.g., the degree of importance is a predetermined value or more) is displayed. Further, the user may be allowed to freely set and customize the combination of images of which a common range is to be displayed.

Further, in the example illustrated in FIG. 10, scales as figures indicating the ranges 1050 and 1090 are displayed in similar forms. Alternatively, the display control unit 150 can display figures indicating respective ranges by changing the display forms of the figures according to the combination of three-dimensional images having a common range. As an example where the display forms of figures, such as scales, are varied, the shapes or the colors of the figures can be changed, or the file names of three-dimensional images in which tomographic images corresponding to each other are present may be displayed next to the figures. Consequently, based on the display forms of figures, such as scales, the user can grasp in which three-dimensional images tomographic images corresponding to each other are present.

In the fifth exemplary embodiment, for ease of description, a description has been given using as an example a case where three three-dimensional images are processed. However, it goes without saying that four or more three-dimensional images can also be similarly processed.

Based on the above, the user can easily grasp the relative positional relationships between two-dimensional images included in three or more three-dimensional images. Particularly, according to the ranges of the positions where two-dimensional images included in three-dimensional images are present, and the combinations of three-dimensional images including these positions in common, the forms of figures indicating these ranges are changed, to display the figures. Consequently, the user can efficiently grasp the relative positional relationships between two-dimensional images included in three-dimensional images.

An information processing apparatus 10 according to a sixth exemplary embodiment switches, according to an operation input provided by the user, a method for displaying the positional relationship between two-dimensional images included in a plurality of three-dimensional images. Consequently, according to medical images to be observed, the user can display the ranges of the positions of two-dimensional images included in the medical images, and therefore can efficiently observe the medical images.

The hardware configuration of the information processing apparatus 10 according to the sixth exemplary embodiment is similar to that according to the exemplary embodiment illustrated in FIG. 12, and therefore, the detailed description of the hardware configuration is omitted here by incorporating the above description.

The functional configuration of the information processing apparatus 10 according to the sixth exemplary embodiment is similar to that according to the first exemplary embodiment illustrated in FIG. 1. Only components having functions different from those illustrated in the first exemplary embodiment are described below, and the detailed description of other components is omitted here by incorporating the above description.

According to an operation input provided by the user, the position acquisition unit 130 determines whether corresponding positional information is to be acquired.

The display control unit 150 displays, on the display unit 13, tomographic images in a first three-dimensional image and a second three-dimensional image. Further, the display control unit 150 displays, on the display unit 13, figures indicating a first range, a second range, an integrated range, a common range, and the positions of the displayed tomographic images by switching the figures according to an operation input provided by the user.

Figure 11:
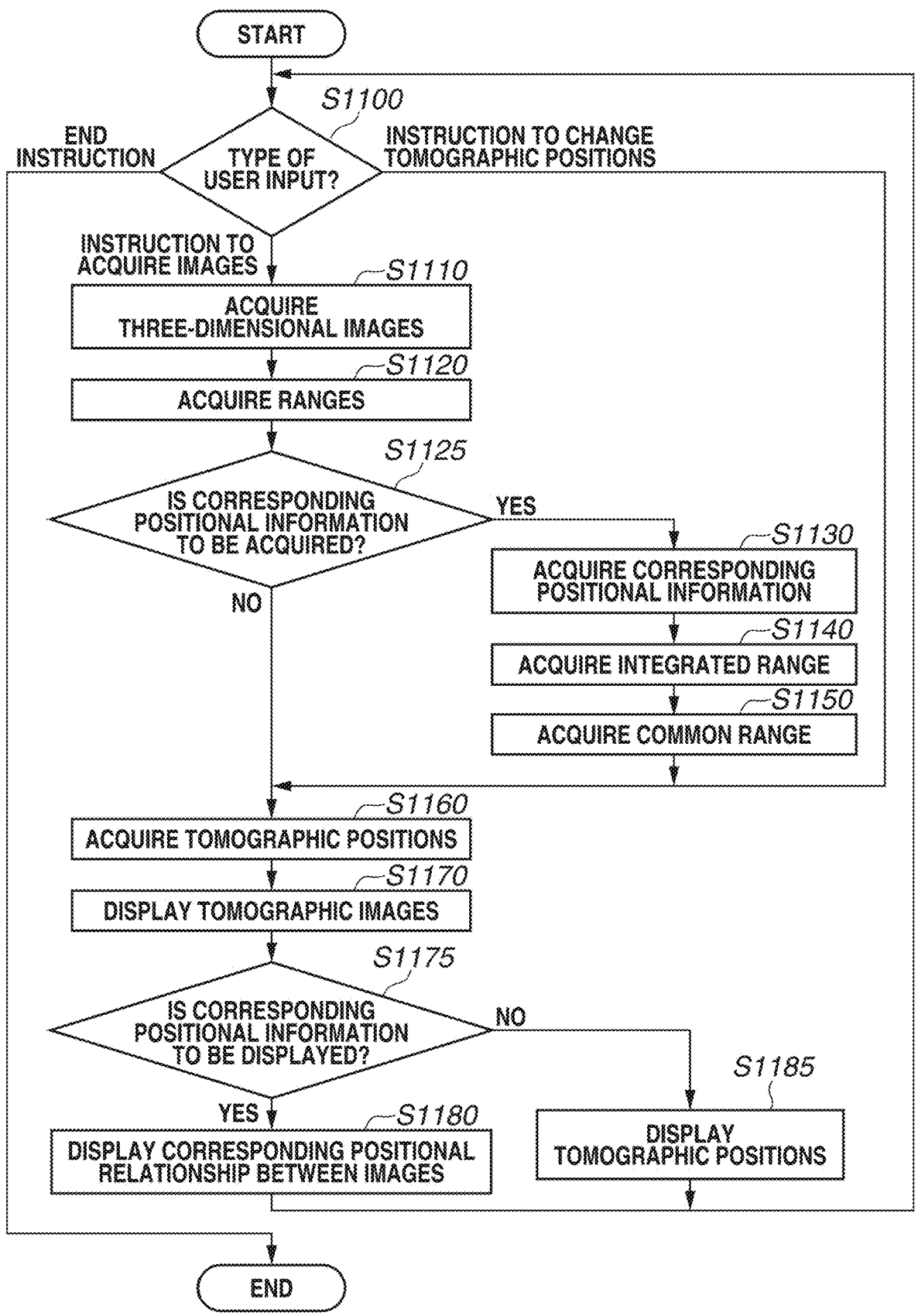
FIG. 11 is a flowchart illustrating an example of processing performed by an information processing apparatus according to a sixth exemplary embodiment.

FIG. 11 is a flowchart illustrating an example of the processing performed by the information processing apparatus 10. The processes of steps S1110, S1120, S1130, S1140, S1150, S1160, S1170, and S1180 are similar to those of steps S210, S220, S230, S240, S250, S260, S270, and S280 in the first exemplary embodiment, and therefore, the detailed description of these processes is omitted here by incorporating the above description.

(Step S1100) (Type of User Input?)

In step S1100, according to the type of an operation input provided by the user through the operation unit 12, the process to be executed next branches. In a case where the type of the operation input is an instruction to acquire images, the processing proceeds to step S1110. In a case where the type of the operation input is an instruction to change tomographic positions, the processing proceeds to step S1160. In a case where the type of the operation input is an end instruction, the processing illustrated in FIG. 11 ends.

(Step S1125) (Is Corresponding Positional Relationship between Images to Be Acquired?)

In step S1125, according to information input to the information processing apparatus 10, the process to be executed next branches. In a case where the number of input three-dimensional images is two (YES in step S1125), the processing proceeds to step S1130. In a case where the number of input three-dimensional images is one (NO in step S1125), the processing proceeds to step S1160.

(Step S1175) (Is Corresponding Positional Relationship between Images to Be Displayed?)

In step S1175, the display control unit 150 determines whether the relative positional relationship between the ranges of the positions where the two-dimensional images included in the three-dimensional images are present is to be displayed. In a case where it is determined that the relative positional relationship is to be displayed (YES in step S1175), the processing proceeds to step S1180. In a case where it is determined that the relative positional relationship is not to be displayed (NO in step S1175), the processing proceeds to step S1185.

For example, in the case of the combination of three-dimensional images of which the corresponding positional information has not been acquired, or in the case of the combination of three-dimensional images of which the common range is not present, the display control unit 150 determines that the relative positional relationship is not to be displayed. For example, in the case of the combination of three-dimensional images of which the common range has been acquired, the display control unit 150 determines that the relative positional relationship is to be displayed. Further, if supplementary information between the three-dimensional images indicates, for example, the same patient, the same modality, or the same captured part, the display control unit 150 can determine that the relative positional relationship is to be displayed.

For example, if the user can perform an operation of simultaneously switching the first and second tomographic positions in conjunction with each other, the display control unit 150 can perform control so that the relative positional relationship is displayed when this conjunction operation is performed. Consequently, in a case where the user simultaneously observes a plurality of images by performing the conjunction operation, the relative positional relationship can be automatically displayed without the user giving an instruction to display the corresponding positional relationship between the images. If, on the other hand, the conjunction operation is not performed, the display control unit 150 can determine that the relative positional relationship is not to be displayed. Further, if the information processing apparatus 10 does not acquire two or more three-dimensional images, the processing can proceed to step S1185 by omitting step S1175.

The user can specify whether the corresponding positional relationship between the images is to be displayed. In this case, according to the type of an operation input provided by the user through the operation unit 12, the process to be executed next is determined. In a case where the user gives an instruction to display the corresponding positional relationship between the images, the processing proceeds to step S1180. In a case where the user gives an instruction not to display the corresponding positional relationship between the images, the processing proceeds to step S1185.

As an example of the operation input provided by the user to give an instruction regarding whether the corresponding positional relationship between the images is to be displayed, a button for the user to give an instruction regarding whether the corresponding positional relationship is to be displayed can be displayed on a screen on which the display control unit 150 displays the tomographic images. If the button is selected, the display control unit 150 receives this selection as an instruction to display the corresponding positional relationship. The display control unit 150 can display a check box or a select box instead of the button.
(Step S1185) (Display Tomographic Positions)

In step S1185, the display control unit 150 displays, on the display unit 13, figures indicating the first and second ranges acquired in step S1120 and the first and second tomographic positions acquired in step S1160.

The figures indicating the first and second ranges are, for example, scales or rectangles indicating the ranges of movement of slider bars. The figures indicating the first and second tomographic positions are, for example, scales or bars. For example, in a case where the first range and the first tomographic position are indicated by scales, the display forms of the scales indicating the first range and the first tomographic position can be different from each other.

In the sixth exemplary embodiment, a description has been given using, as an example, a case where two three-dimensional images are processed similarly to the first exemplary embodiment. Alternatively, the number of three-dimensional images to be input can be three or more. In this case, in steps S1110, S1120, S1130, S1140, S1150, S1160, S1170, and S1180, processes similar to those of steps S910, S920, S930, S940, S950, S960, S970, and S980 in the fifth exemplary embodiment are performed.

In the first to sixth exemplary embodiments, descriptions have been given using, as examples, cases where, as illustrated in FIGS. 4A to 4D and 10, figures indicating a first range, a second range, and an integrated range are displayed on medical images. The present disclosure, however, is not limited to this. The figures can be displayed in any places on the display unit 13 so long as the ranges indicated by the respective figures and the medical images corresponding to each other can be distinguished.

The present disclosure can also be achieved by the process of supplying a program for achieving one or more functions of the above exemplary embodiments to a system or an apparatus via a network or a storage medium, and of causing one or more processors of a computer of the system or the apparatus to read and execute the program. Further, the present disclosure can also be achieved by a circuit or circuitry (e.g., an ASIC) for achieving the one or more functions.

The information processing apparatus according to each of the above exemplary embodiments can be achieved as a single apparatus, or may be achieved in a form in which the above processing is executed by combining a plurality of apparatuses so that the plurality of apparatuses can communicate with each other. Both cases are included in the exemplary embodiments of the present disclosure. The above processing can be executed by a common server apparatus or server group. A plurality of apparatuses included in an information processing apparatus and an information processing system may only need to be able to communicate with each other at a predetermined communication rate, and is not needed to exist in the same facility or the same country.

The exemplary embodiments of the present disclosure include a form in which a program of software for achieving the functions of the above exemplary embodiments is supplied to a system or an apparatus, and a computer of the system or the apparatus reads and executes the code of the supplied program.

Thus, a program code itself installed in a computer to achieve the processing according to the exemplary embodiments by the computer is also one of the exemplary embodiments of the present disclosure. Further, the functions of the above exemplary embodiments can also be achieved by part or all of actual processing performed by an operating system (OS) operating on a computer based on an instruction included in a program read by the computer.

Forms obtained by appropriately combining the above exemplary embodiments are also included in the exemplary embodiments of the present disclosure.

According to the information processing apparatus according to each of the exemplary embodiments of the present disclosure, it is possible to easily grasp the relative positional relationship between cross-sectional images in respective pieces of volume data.

Other Embodiments

Embodiment(s) of the present disclosure can also be realized by a computerized configuration(s) of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits or circuitry (e.g., application specific integrated circuit (ASIC)) for performing the functions of one or more of the above-described embodiment(s), and by a method performed by the computerized configuration(s) of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computerized configuration(s) may comprise one or more processors, one or more memories (e.g., central processing unit (CPU), micro processing unit (MPU)), and may include a network of separate computers or separate processors to read out and execute the computer executable instructions. The computer executable instructions may be provided to the computerized configuration(s), for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

This application claims the benefit of priority from Japanese Patent Application No. 2017-079433, filed Apr. 13, 2017, which is hereby incorporated by reference herein in its entirety.

What is claimed is:

1. An information processing apparatus comprising:
at least one memory storing instructions; and
at least one processor that when executing the instructions, causes the information processing apparatus to:
based on information regarding tomographic positions of two-dimensional images included in a first three-dimensional image and two-dimensional images included in a second three-dimensional image different from the first three-dimensional image, acquire information regarding a first range, which is a range of tomographic positions where the two-dimensional images included in the first three-dimensional image are present, and a second range, which is different from the first range and is a range of tomographic positions where the two-dimensional images included in the second three-dimensional image are present;
determine whether or not a user is able to perform an operation of simultaneously switching a first tomographic position in the first three-dimensional image and a second tomographic position in the second three-dimensional image; and
based on the determination, display, on a display unit, a first figure indicating the first range such that an area, in the first range, included in the second range is distinguishable, and display, on the display unit, a second figure indicating a tomographic position of the two-dimensional image included in the first three-dimensional image and displayed on the display unit, wherein the first figure, the area in the first range and the second figure are displayed such that a relative position therebetween is indicated, and
wherein the operation of switching the first and second tomographic positions is performed in conjunction with an operation of moving the second figure relative to the first figure.

2. The information processing apparatus according to claim 1, wherein the at least one processor further causes the information processing apparatus to acquire, as the first range, a range of tomographic positions where the two-dimensional images are present, in a direction orthogonal to the two-dimensional images included in the first three-dimensional image, and acquire, as the second range, a range of tomographic positions where the two-dimensional images are present, in a direction orthogonal to the two-dimensional images included in the second three-dimensional image.

3. The information processing apparatus according to claim 1,
wherein the at least one processor further causes the information processing apparatus to acquire information regarding a third range, which is a range of tomographic positions of two-dimensional images included in either of the first and second three-dimensional images, and
wherein, in a figure indicating the third range, the information processing apparatus displays, in the third range, an area corresponding to the first range, an area corresponding to the second range, and a common area of the first and second ranges such that the areas are distinguishable from each other.

4. The information processing apparatus according to claim 1, wherein the at least one processor further causes the information processing apparatus to display, on the display unit, a figure indicating a common range of the first and second ranges.

5. The information processing apparatus according to claim 1, wherein in a case where the first and second ranges have a common range according to the information regarding the first range and the information regarding the second range, the information processing apparatus displays a figure indicating the common range.

6. The information processing apparatus according to claim 1, wherein the at least one processor further causes the information processing apparatus to display the first figure.

7. The information processing apparatus according to claim 1, wherein the at least one processor further causes the information processing apparatus to:
perform registration between the two-dimensional images included in the first three-dimensional images and the two-dimensional images included in the second three-dimensional images, and
acquire the first range and the second range based on a result of the registration.

8. The information processing apparatus according to claim 1, wherein the at least one processor further causes the information processing apparatus to:
based on presence or absence of a corresponding positional information between the first three-dimensional image and the second three-dimensional image, determine whether or not to display, on the display unit, a third figure indicating a tomographic position of a two-dimensional image displayed on the display unit, and
based on the determination, display, on the display unit, the first figure and the third figure.

9. The information processing apparatus according to claim 1, wherein the at least one processor further causes the information processing apparatus to:

based on supplementary information associated with the first three-dimensional image and supplementary information associated with the second three-dimensional image, determine whether or not to display, on the display unit, a third figure indicating a tomographic position of a two-dimensional image displayed on the display unit.

10. The information processing apparatus according to claim 9, wherein the supplementary information includes information about at least one of a patient identifier (ID), an image-capturing modality, and a captured part.

11. The information processing apparatus according to claim 1, wherein the first range and the second range are displayed to be close to each other.

12. The information processing apparatus according to claim 1, wherein the at least one processor further causes the information processing apparatus to:

display, on a display unit, a third figure indicating the second range such that an area, in the second range, included in the first range is distinguishable, and display, on the display unit, a fourth figure indicating a tomographic position of the two-dimensional image included in the second three-dimensional image and displayed on the display unit, wherein the third figure, the area in the first range and the fourth figure are displayed such that a relative position therebetween is indicated.

13. The information processing apparatus according to claim 12, wherein the at least one processor further causes the information processing apparatus to:

display the first figure, the area in the first range and the third figure such that a relative position therebetween is indicated.

14. An information processing method comprising:

based on information regarding tomographic positions of two-dimensional images included in a first three-dimensional image and two-dimensional images included in a second three-dimensional image different from the first three-dimensional image, acquiring information regarding a first range, which is a range of tomographic positions where the two-dimensional images included in the first three-dimensional image are present, and a second range, which is different from the first range and is a range of tomographic positions where the two-dimensional images included in the second three-dimensional image are present;

determining whether or not a user is able to perform an operation of simultaneously switching a first tomographic position in the first three-dimensional image and a second tomographic position in the second three-dimensional image; and displaying, on a display unit, a first figure indicating the first range such that an area, in the first range, included in the second range is distinguishable, and displaying, on the display unit, a second figure indicating a tomographic position of the two-dimensional image included in the first three-dimensional image and displayed on the display unit, based on the determination, wherein the first figure, the area in the first range and the second figure are displayed such that a relative position therebetween is indicated, and wherein the operation of switching the first and second tomographic positions is performed in conjunction with an operation of moving the second figure relative to the first figure.

15. A non-transitory storage medium for causing a computer to execute an information processing method comprising:

based on information regarding tomographic positions of two-dimensional images included in a first three-dimensional image and two-dimensional images included in a second three-dimensional image different from the first three-dimensional image, acquiring information regarding a first range, which is a range of tomographic positions where the two-dimensional images included in the first three-dimensional image are present, and a second range which is different from the first range and is a range of tomographic positions where the two-dimensional images included in the second three-dimensional image are present;

determining whether or not a user is able to perform an operation of simultaneously switching a first tomographic position in the first three-dimensional image and a second tomographic position in the second three-dimensional image; and displaying, on a display unit, a first figure indicating the first range such that an area, in the first range, included in the second range is distinguishable, and displaying, on the display unit, a second figure indicating a tomographic position of the two-dimensional image included in the first three-dimensional image and displayed on the display unit, based on the determination, wherein the first figure, the area in the first range and the second figure are displayed such that a relative position therebetween is indicated, and wherein the operation of switching the first and second tomographic positions is performed in conjunction with an operation of moving the second figure relative to the first figure.

16. An information processing apparatus comprising:

at least one memory storing instructions; and at least one processor that when executing the instructions, causes the information processing apparatus to:

based on information regarding tomographic positions of first two-dimensional images included in a first three-dimensional image and second two-dimensional images included in a second three-dimensional image, acquire information regarding a first range, which is a range of tomographic positions where the first two-dimensional images are present, and a second range, which is a range of tomographic positions where the second two-dimensional images are present;

determine whether there is a range common to the first range and the second range; and display, on a display unit, a first figure indicating the first range, a second figure indicating a tomographic position of the two-dimensional image included in the first three-dimensional image and a third figure indicating the common range in the first range based on a result of determination such that a relative position between the first figure, the second figure and the third figure is indicated, and wherein an operation of switching the tomographic position of the two-dimensional image is performed in conjunction with an operation of moving the second figure relative to the first figure.

17. An information processing apparatus comprising:

at least one memory storing instructions; and at least one processor that when executing the instructions, causes the information processing apparatus to:

based on information regarding tomographic positions of first two-dimensional images included in a first three-dimensional image and second two-dimensional images included in a second three-dimensional image, acquire information regarding a first range, which is a range of tomographic positions where the first two-dimensional images are present, and a second range, which is a range of tomographic positions where the second two-dimensional images are present;

determine whether there is a range common to the first range and the second range; and based on a result of determination, display, on a display unit, a first figure indicating the first range and a second figure indicating a tomographic position of the two-dimensional image included in the first three-dimensional image such that a relative position therebetween is indicated, wherein the first figure is displayed on the display unit such that the common range in the first range and a range other than the common range are displayed in different states, and wherein an operation of switching the tomographic position of the two-dimensional image is performed in conjunction with an operation of moving the second figure relative to the first figure.

\* \* \* \* \*